(12) United States Patent
Rinner

(10) Patent No.: US 9,649,137 B2
(45) Date of Patent: May 16, 2017

(54) SPINAL STABILIZATION SYSTEM

(71) Applicant: James A. Rinner, Franksville, WI (US)

(72) Inventor: James A. Rinner, Franksville, WI (US)

( * ) Notice: Subject to any disclaimer, the term of this patent is extended or adjusted under 35 U.S.C. 154(b) by 168 days.

(21) Appl. No.: 14/289,940

(22) Filed: May 29, 2014

(65) Prior Publication Data
US 2015/0073484 A1 Mar. 12, 2015

Related U.S. Application Data

(63) Continuation of application No. 14/198,447, filed on Mar. 5, 2014, and a continuation of application No. 14/271,902, filed on May 7, 2014.

(60) Provisional application No. 61/875,239, filed on Sep. 9, 2013.

(51) Int. Cl.
*A61B 17/70* (2006.01)
*A61B 17/86* (2006.01)

(52) U.S. Cl.
CPC ...... *A61B 17/7052* (2013.01); *A61B 17/7032* (2013.01); *A61B 17/7034* (2013.01); *A61B 17/7037* (2013.01); *A61B 17/7046* (2013.01); *A61B 17/7056* (2013.01); *A61B 17/7076* (2013.01); *A61B 17/8605* (2013.01); *A61B 17/7011* (2013.01); *A61B 17/7035* (2013.01); *A61B 17/861* (2013.01)

(58) Field of Classification Search
CPC ............ A61B 17/7032; A61B 17/7034; A61B 17/7035; A61B 17/7037; A61B 17/7046
USPC .................. 606/246–278, 300–321
See application file for complete search history.

(56) References Cited

U.S. PATENT DOCUMENTS

| | | | | |
|---|---|---|---|---|
| 6,010,503 A | * | 1/2000 | Richelsoph | A61B 17/7032 606/278 |
| 2006/0036242 A1 | * | 2/2006 | Nilsson | A61B 17/7037 606/264 |
| 2007/0225711 A1 | * | 9/2007 | Ensign | A61B 17/7037 606/86 A |
| 2009/0105716 A1 | * | 4/2009 | Barrus | A61B 17/7032 606/301 |
| 2009/0105770 A1 | * | 4/2009 | Berrevoets | A61B 17/7032 606/308 |
| 2010/0114170 A1 | * | 5/2010 | Barrus | A61B 17/7037 606/264 |
| 2010/0160977 A1 | * | 6/2010 | Gephart | A61B 17/7035 606/305 |
| 2010/0234902 A1 | * | 9/2010 | Biedermann | A61B 17/7037 606/305 |
| 2011/0160778 A1 | * | 6/2011 | Elsbury | A61B 17/7037 606/305 |
| 2014/0172018 A1 | * | 6/2014 | Gephart | A61B 17/7035 606/279 |
| 2014/0277155 A1 | * | 9/2014 | Barrus | A61B 17/7056 606/276 |

(Continued)

FOREIGN PATENT DOCUMENTS

WO WO 2008048953 A2 * 4/2008 ......... A61B 17/7032

*Primary Examiner* — Ellen C Hammond
(74) *Attorney, Agent, or Firm* — Brainspark Associates, LLC

(57) ABSTRACT

The present invention is directed to a spinal implant system that incorporates unique snap, or spring loaded, features to assist the surgeon in the placement of screws, rods, hooks and transverse connectors. The poly-axial movement also uses a more direct loading lower saddle into the bone screw to improve locking of the construct.

19 Claims, 22 Drawing Sheets

(56) References Cited

U.S. PATENT DOCUMENTS

2015/0073488 A1\* 3/2015 Rinner ............... A61B 17/7052
606/305

\* cited by examiner

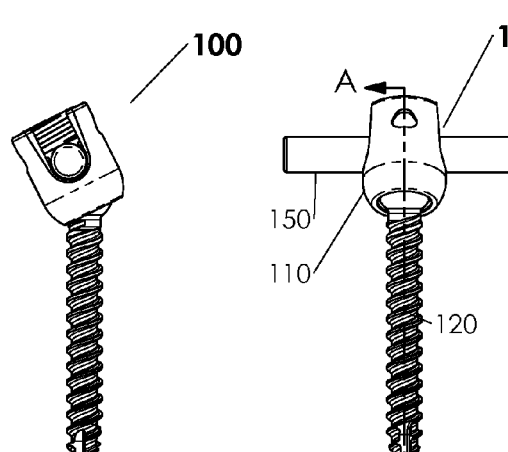
FIG. 4
FIG. 5
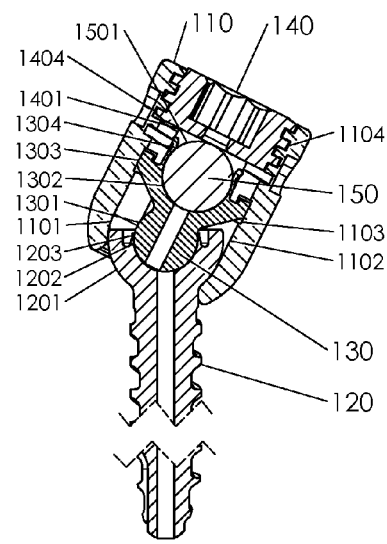
FIG. 6
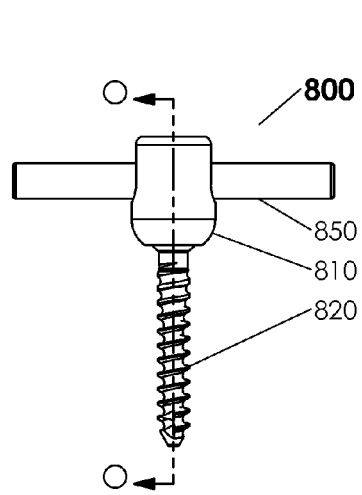
PRIOR ART
FIG. 7
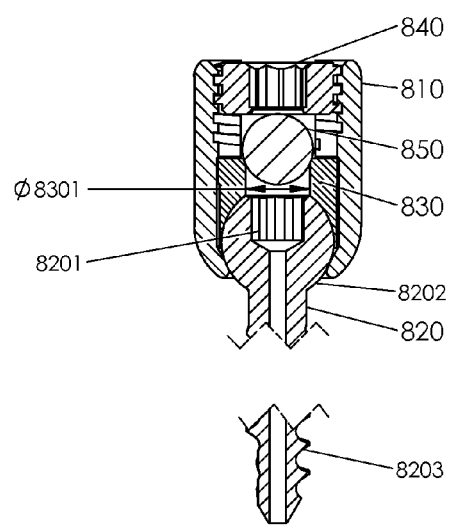
PRIOR ART
FIG. 8

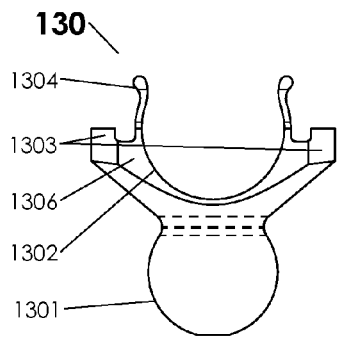
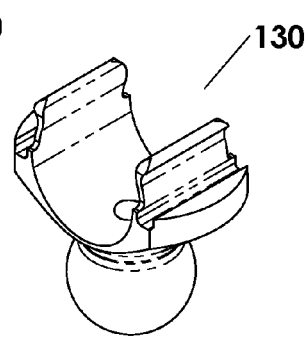
FIG. 24    FIG. 25    FIG. 26
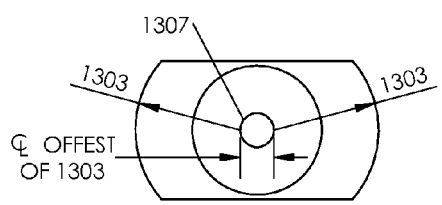
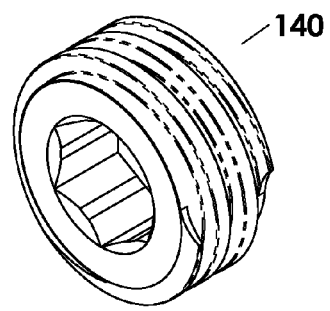
FIG. 27    FIG. 28
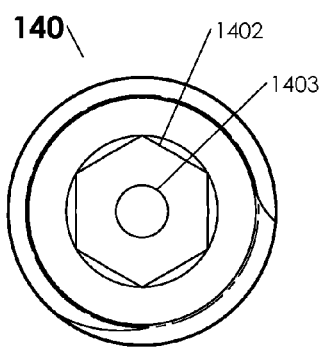
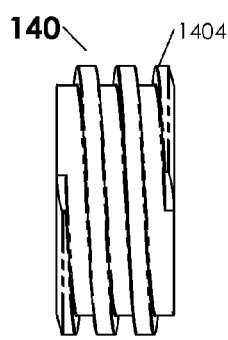
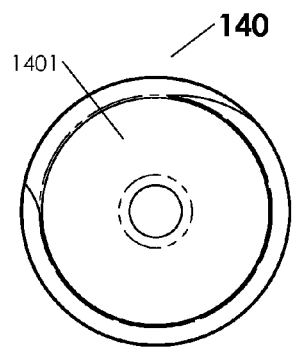
FIG. 29    FIG. 30    FIG. 31

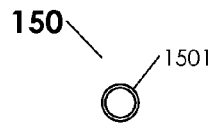
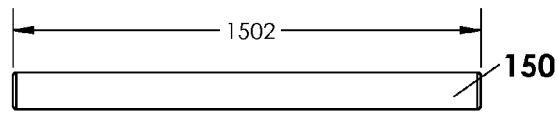
FIG. 69
FIG. 70
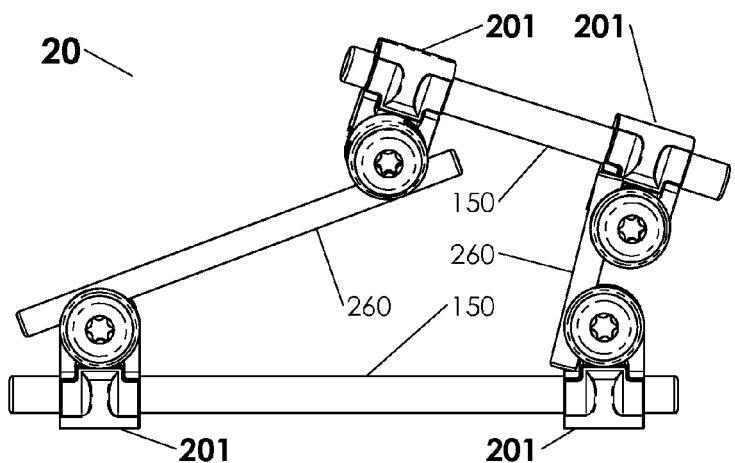
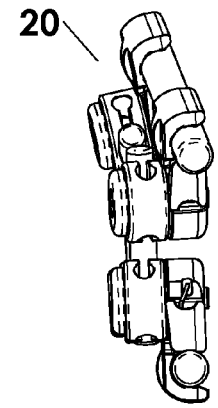
FIG. 71
FIG. 72
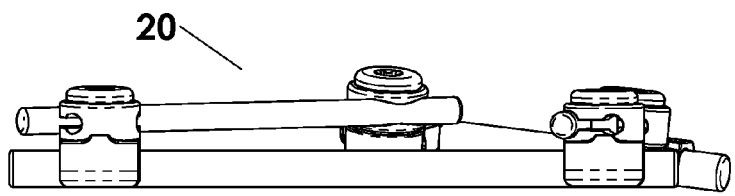
FIG. 73
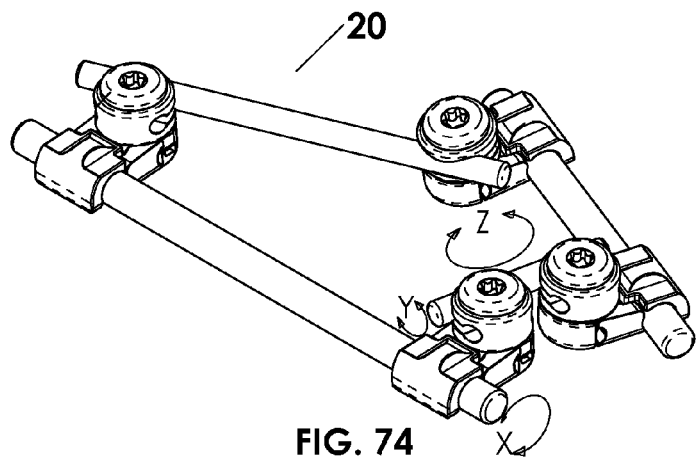
FIG. 74

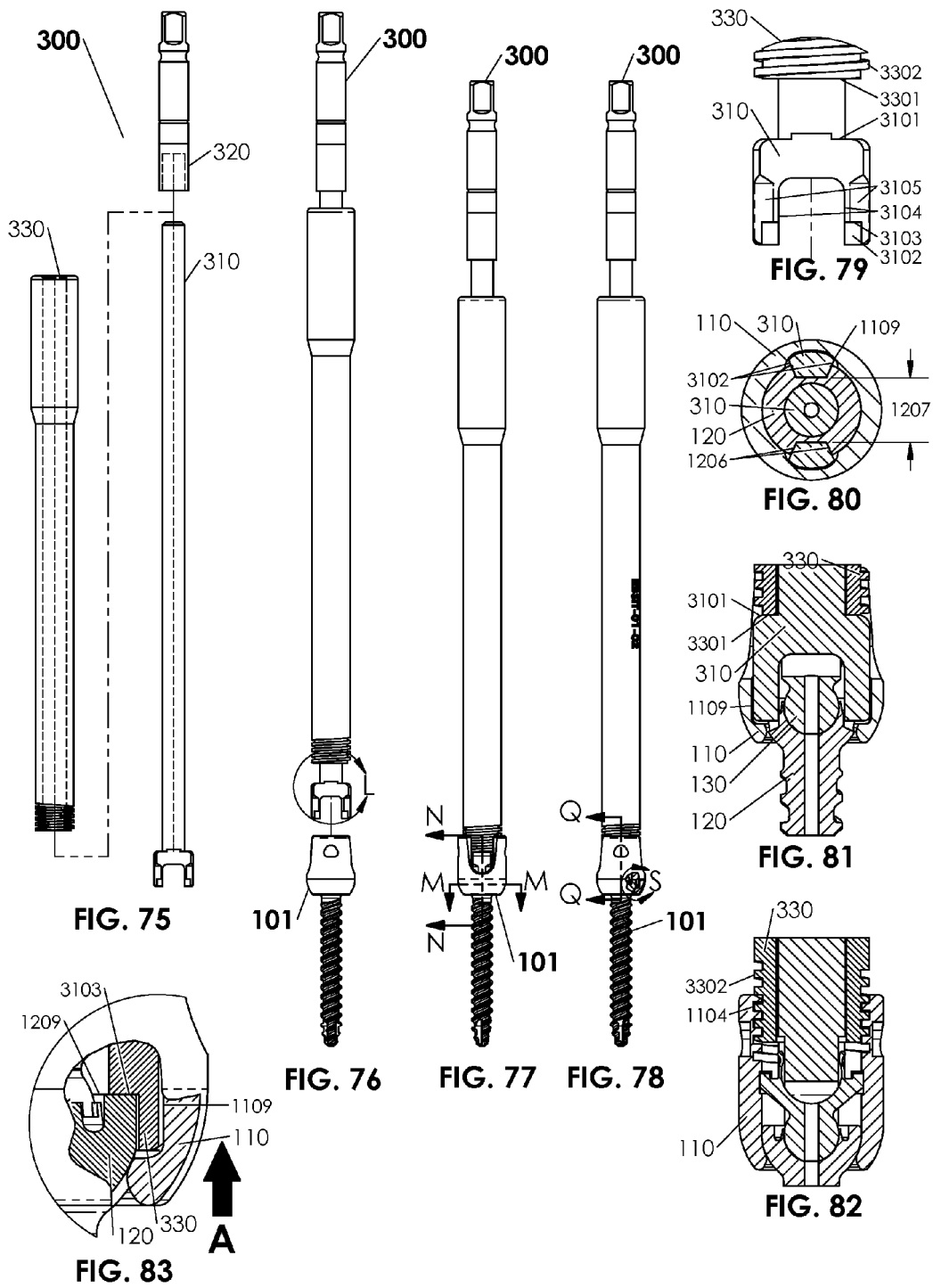

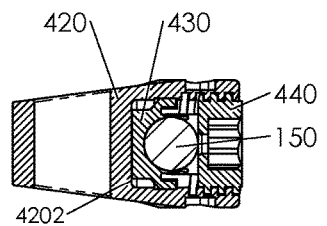
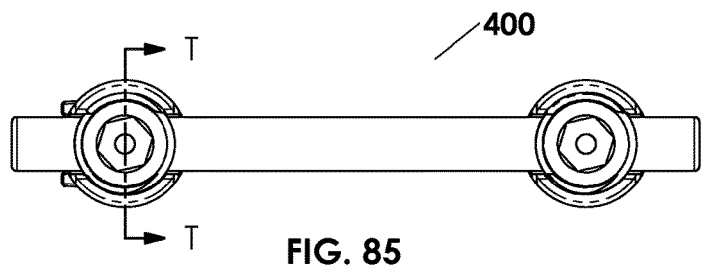
FIG. 84  FIG. 85
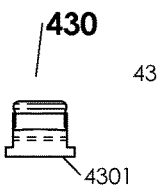
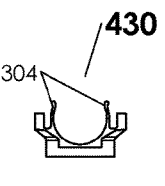
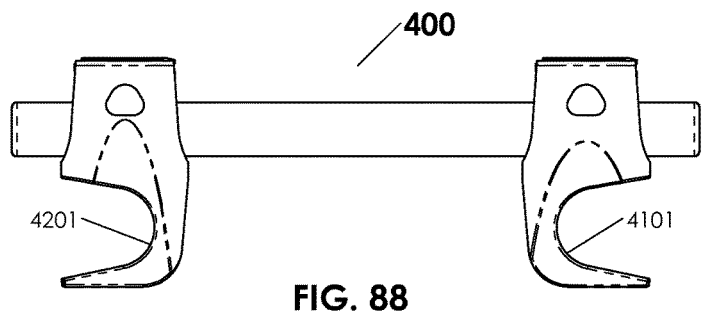
FIG. 86  FIG. 87  FIG. 88
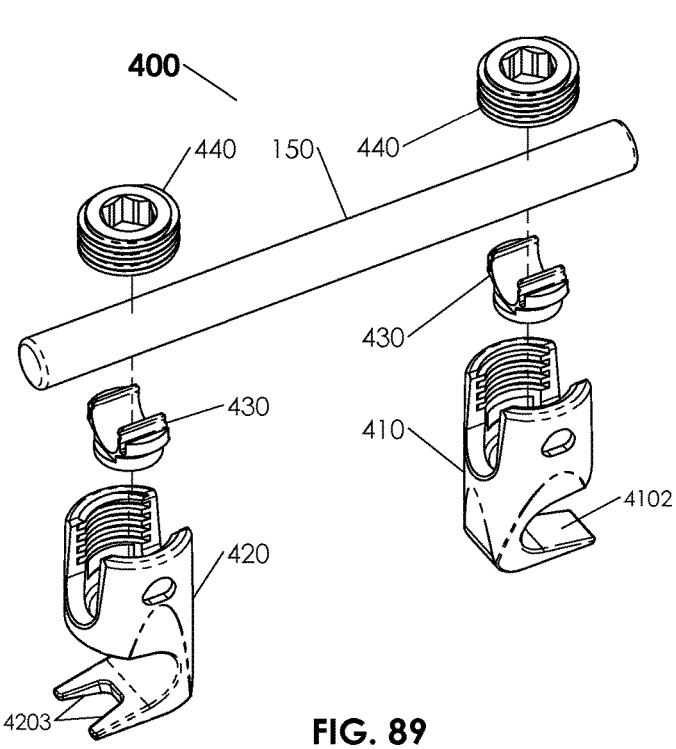
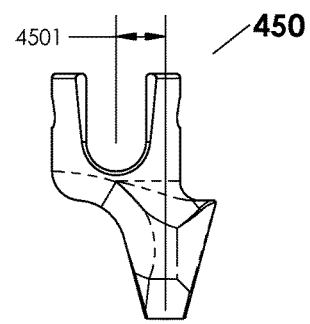
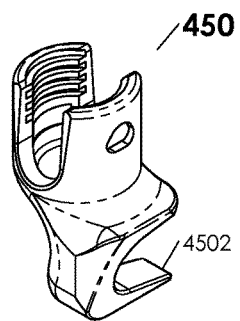
FIG. 89  FIG. 90  FIG. 91

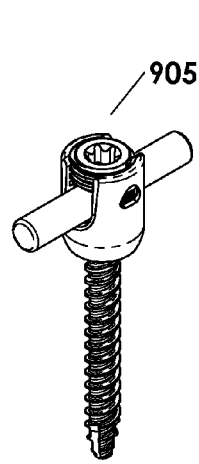
FIG. 106
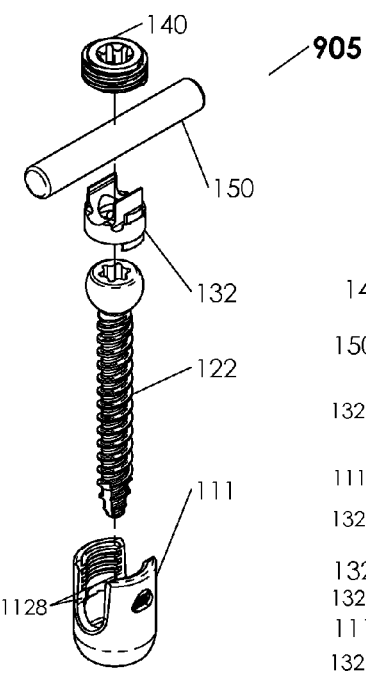
FIG. 107
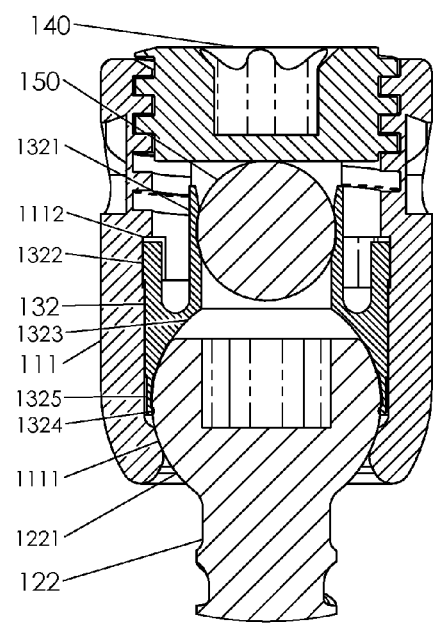
FIG. 110
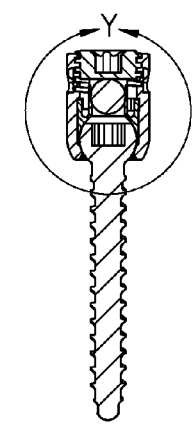
FIG. 108
FIG. 109

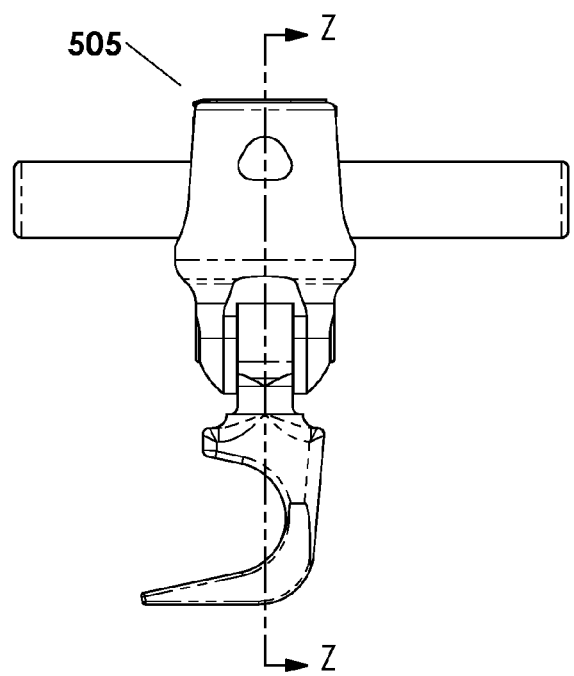
FIG. 119
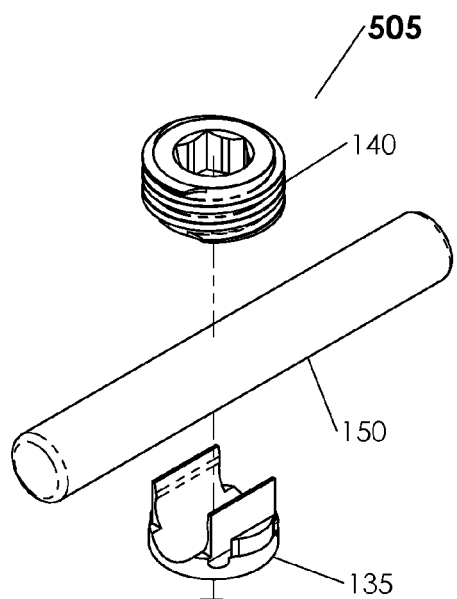
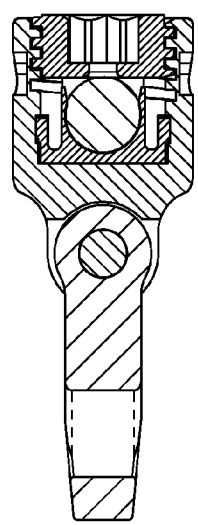
FIG. 120
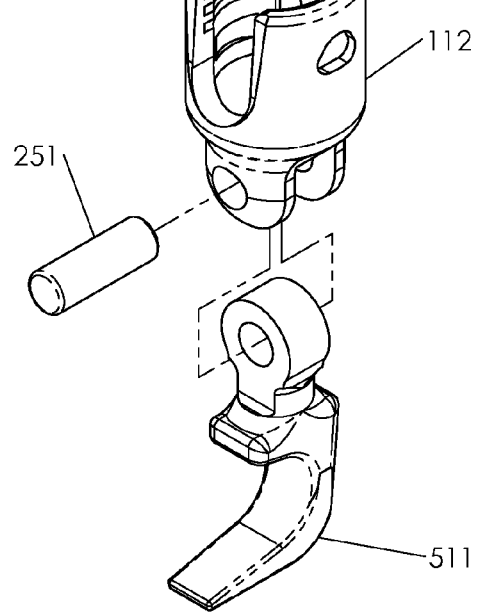
FIG. 121

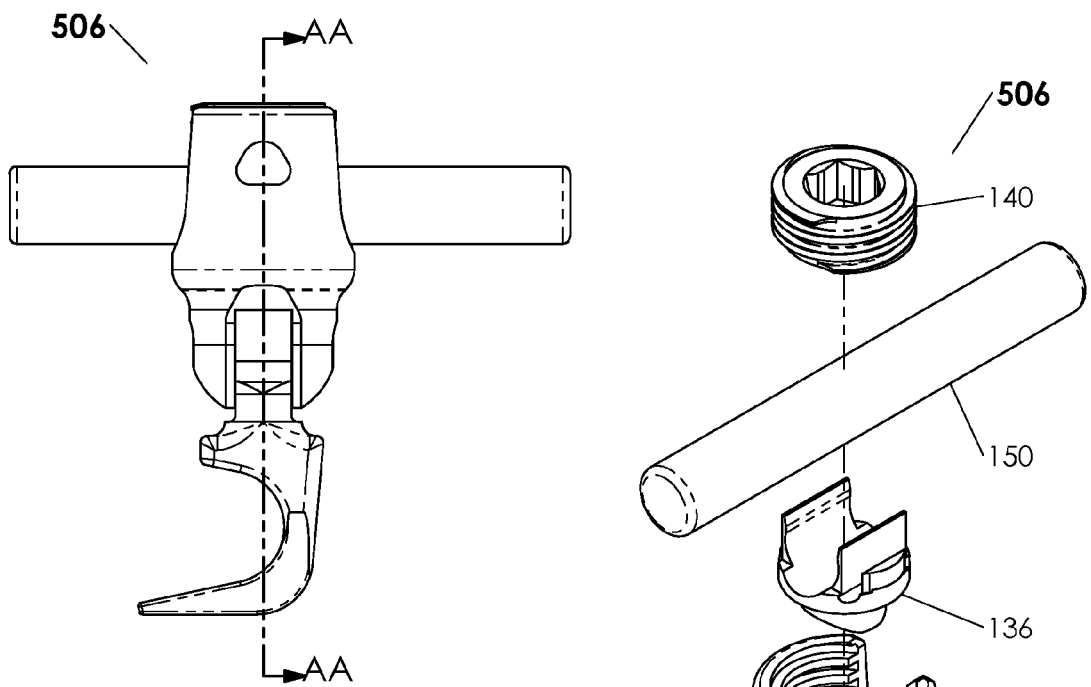
FIG. 122
FIG. 124
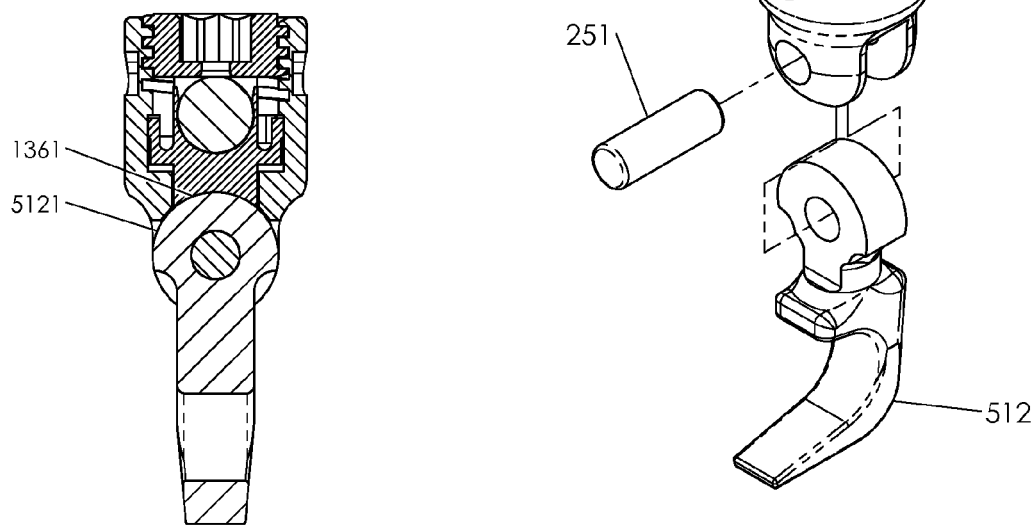
FIG. 123

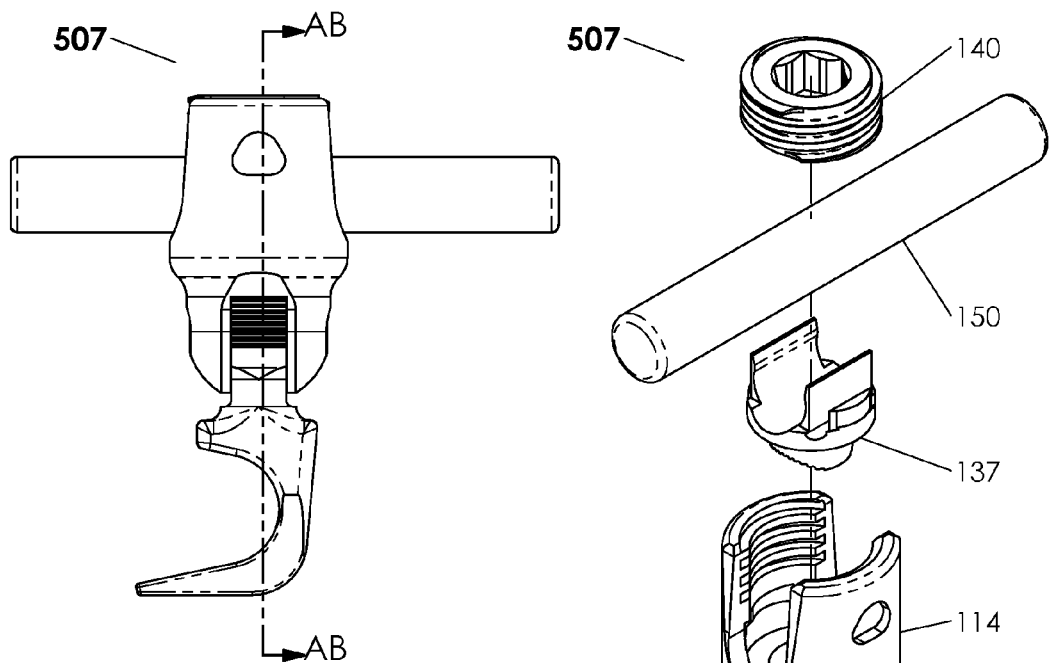
FIG. 125
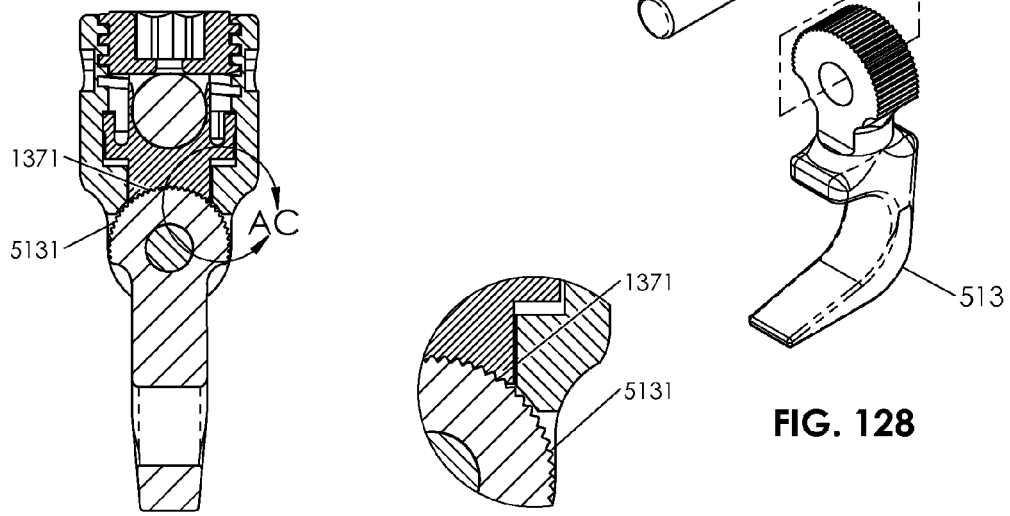
FIG. 126  FIG. 127  FIG. 128

SPINAL STABILIZATION SYSTEM

CROSS-REFERENCE TO OTHER APPLICATIONS

This application is a continuation application of U.S. patent application Ser. No. 14/271,902 entitled "Spinal Stabilization System," filed May 7, 2014, and U.S. patent application Ser. No. 14/198,447 entitled "Spinal Stabilization System," filed Mar. 5, 2014, and further claims the benefit of U.S. Provisional Patent Application Ser. No. 61/875,239 entitled "Spinal Stabilization System," filed Sep. 9, 2013, the disclosures of which are each incorporated herein by reference in their entireties.

TECHNICAL FIELD

The present invention relates to devices and methods for assembling and adjusting orthopedic constructs connected to bony anatomy of a patient. More particularly, the present invention relates to improved devices and methods for pedicle screw and rod-based fixation assembly systems that utilize monoaxial and/or polyaxial bone screws, such as spinal fixation systems and associated components.

BACKGROUND OF THE INVENTION

A wide variety of surgical techniques and associated instrumentation systems have been developed for correcting degenerative disc disease, spondylolisthesis, spinal deformities, or other spinal conditions through minimally invasive or invasive spinal surgery. Spinal correction during surgery may be performed by a variety of methodologies that may frequently require stabilizing a portion of the spine to allow bone or other tissue growth between vertebral bodies such that a portion of the spine is stabilized into a solitary unit and/or specified shape.

Numerous surgical instrumentation systems have been developed and commercialized for stabilizing and correcting spinal conditions and/or deformities. In one of the most popular types of spinal stabilization systems, pedicle screw and rods systems, two or more screw assemblies are secured into bony structures of the a patient's vertebrae, and a rod or other device is connected between the screw assemblies, typically disposed longitudinally along the length of the spinal segment to anchor the two or more vertebral bodies relative to each other. The rod can be arranged in a variety of positions and/or configurations (including the use of multiple rods and/or cross-bars, where desired) according to the patient's anatomy and/or the correction desired. In many cases, the patient's anatomy and/or the desired surgical correction required can require aligning one or more rods and associated pedicle screws at various multi-axial angles and/or orientations along the length of the portion of the spinal segment.

Unfortunately, existing pedicle screw systems are typically rather large and bulky, and the modularity and/or flexibility designed into the components in many of these systems can render the systems difficult for a surgeon to use effectively. For example, the various feature that facilitate the assembly of different size and/or shape rod and screw constructs, and eventual "locking" of the components together (i.e., the pedicle screw assembly and the rod) to specified orientations, shapes and/or multi-axial angles (prior to fixation) can be difficult and/or impossible to assemble within a wound. Moreover, where components have been preassembled, such as where a pedicle screw subassembly includes a tulip head pre-connected with a mono-axially and/or poly-axially adjustable bone screw shank, the tulip head will desirably move relative to the shank. In many such instances, however, manufacturing and/or assembly of the tulip head, relevant inserts and/or the shank itself can result in a subassembly where the shank/head is loose and can "flop" around, making it extremely difficult for the surgeon to assemble the construct and/or tighten the remaining components together. Alternatively, the tulip head may be too tight relative to the shank, rending it difficult and/or impossible for the surgeon to adjust the assembly by hand (prior to fixation).

Assembly difficulties can also be experienced when positioning and/or connecting one or more of the rods to the implanted pedicle screws. Because patient anatomy is unique, which can often be compounded by significant preoperative deformity, rarely do the implanted pedicle screw heads conveniently "line up" in a uniform manner. In fact, implanted screws can often be significantly displaced from adjacent screws. Also, when the surgeon places a rod into pedicle screws, the rod may slide to an undesired position or otherwise be displaced or moved before the surgeon is ready for tightening the remaining components together. This may inconvenience the surgeon and might require surgical assistants, technicians or staff members to properly orient the pedicle screw assembly and maintain the rod position while the surgeon fully tightens all of the components together. In many cases, the proper fixation of the stabilization system particularly depends on the surgeon and/or staff to properly assemble the rod and the pedicle system, orient the pedicle screw system, and/or position the rod properly to effectively lock the components together with the set screw, otherwise no amount of tightening the set screw will fully or effectively lock the pedicle screw assembly together—i.e., the floppiness remains and the rod may move axially to an undesired position.

SUMMARY OF THE INVENTION

One aspect of the present invention includes a recognition of a need for spinal stabilization systems that can be partially and/or fully "assembled" within the surgical wound in an "unlocked" (or "partially-unlocked") configuration, which allows for adjustment of the various components prior to final securement and "locking" of the construct. Moreover, various embodiments described herein include audible and/or tactile indicators or "assurances" to the surgeon and/or staff that a "temporary" and/or "provisional" connection between various modular components has been initiated, with these "temporary" and/or "provisional" connections not requiring removal and/or modification before the pedicle screw system and associated rods can be securely locked into a desired axial position, angle, and/or orientation. The disclosure is also directed to several alternative designs, materials and methods of assembling polyaxial bone anchor structures and assemblies.

Various embodiments described herein disclose screw (and/or other fixation element types such as hook, pins and/or loops) and rod fixation systems incorporating components (including modular and/or interchangeable components and/or subcomponents) that can be adjusted in-situ and that provide a strong, effective and secure locking of the screws, rods and/or other fixation elements in a desired configuration, position, orientation and/or angle when desired by a surgeon. In addition, the various embodiments significantly reduce the size and/or number of components to provide for simpler, more effective, more durable and/or less cumbersome devices for fixation of anatomical structures.

In one exemplary embodiment, a spinal stabilization construct can comprise a tulip body, a bone screw, a lower saddle or insert, a support rod, and a set screw. The tulip body may include arms defining a slot and/or channel therebetween (sized for receiving the support rod), a base portion defining an opening to receive a shank portion of the bone screw and a surface adjacent the opening for supporting the head of the bone screw, a pocket to receive the lower saddle insert and internal threading to accommodate the set screw. The lower saddle insert may include one or more locking features that secure the insert into the tulip body, and can further include various detent, "snap-fit" and/or frictional coupling features operable between the support rod and the insert (within the tulip body) as well as between the bone screw and the insert (within the tulip body), while allowing relative movement and/or adjustability between the various modular components (even when anchored to the vertebral bodies) prior to ultimate fixation and/or "immobilization" of the spinal stabilization construct.

In another embodiment, the spinal stabilization system may comprise a monoaxial hook pedicle screw system. The monoaxial hook pedicle screw system may include a tulip body having one or more hooked shaped projections, a support rod, a lower saddle insert, and a set screw. The hook tulip body may include arms defining a slot and/or channel therebetween sized for receiving the support rod, a base portion defining an opening to receive a targeted bone segment, and at least one pocket to receive tabs from the lower saddle insert. Alternatively, the hook tulip body may contain an offset base portion, where the base portion may be axially distanced away or adjacent to the arms that define a slot and/or channel therebetween. Furthermore, the lower saddle insert may contain a plurality of frictional or other components that can operate to "lock" the insert to the support rod and the hook tulip body.

In another embodiment, the spinal stabilization system may comprise a polyaxial hook pedicle screw system. The polyaxial hook pedicle screw system may include a bifurcated and/or clevised tulip body, a support rod, a lower saddle insert, a pivotal hook portion, and a set screw. The hook tulip body may include arms defining a slot and/or channel therebetween sized for receiving the support rod, a bifurcated and/or clevised base portion defining an opening to receive a pivotal bone hook, and at least one pocket to receive tabs from the lower saddle insert. The lower saddle insert may contain a plurality of frictional or other components that will operate to "lock" the insert to the support rod and the hook tulip body. Furthermore, the pivotal hook may include a pivot base portion that may be removably connected to the opening of the bifurcated and/or clevised tulip body, and a hook base portion that may be removably connected to a targeted bone segment. The pivot base portion may be designed with multiple shape configurations and surfaces to allow desired polyaxial orientation and preciseness (i.e., round, arched, smooth surface, and/or ratcheted surface, etc).

In another alternative embodiment, the spinal stabilization system may comprise a multi-level transverse connector system. The multi-level transverse connector system may include a plurality of transversely-positioned pedicle screw systems that facilitate anchoring of one or more pedicle screw constructs to various targeted bone segment configurations. Exemplary transverse pedicle screw system components may include a connector body, pivot clamp, rod clamp, clamp screw, spring shaft and/or connector rod. The connector rods may be supplied in different lengths, shapes and/or sizes to accommodate various orientations, spinal anatomy and desired correction.

In another alternative embodiment, the spinal stabilization systems may comprise an angled polyaxial pedicle screw systems. Angled polyaxial pedicle screw systems may include a curved and/or bent support rod in conjunction with multiple tilted and/or angled tulip bodies, associated lower saddle inserts, and/or set screws. The bent support rod facilitates the placement of pedicle screw subassemblies in bony structures adjacent to each other, such as into pedicles of adjacent vertebral bodies, to achieve a desired curvature, preciseness, and/or anchoring of the anatomy. The bent support rod may be already supplied in a desired bent angle or may be bent in-situ prior to final anchoring of the system. If desired, tilted and/or angled tulip bodies can be provided that facilitate the placement of pedicle screw subassemblies in very close proximity and/or at relative angles where traditional tulip body designs may be precluded, such as where the tulip bodies would interfere and/or overlap with each other.

In another alternative embodiment, the various spinal stabilization systems described herein could include a variety of tools and/or surgical techniques for facilitating anchoring and/or attachment of the systems to targeted bony structures and/or anatomical bone segments. Exemplary tool designs could include screw drivers, support rod cutters, support rod benders and/or drivers that may be supplied as a kit with the spinal stabilization systems or separately upon request and/or need by the surgeon.

BRIEF DESCRIPTION OF THE DRAWINGS

The present invention should be better understood in conjunction with the detailed description below and the accompanying drawings.

FIG. 4 depicts a side view of the pedicle screw subassembly of FIG. 2 with the tulip head tilted;

FIG. 5 depicts a front view of the pedicle screw subassembly of FIG. 4;

FIG. 6 depicts a magnified cross-sectional side view of the pedicle screw subassembly of FIG. 5, taken along line A-A;

FIG. 7 is an side view of one embodiment of a prior art pedicle screw system;

FIG. 8 depicts a magnified side cross-sectional section view along line C-C of the prior art pedicle screw system of FIG. 7;

FIGS. 24, 25 and 27 depicts various planar views of one embodiment of the lower saddle;

FIG. 26 depicts a perspective view of the lower saddle of FIG. 24;

FIG. 28 depicts a perspective view of one embodiment of a set screw;

FIGS. 29 through 31 depict various planar views of the set screw of FIG. 28;

FIG. 69 depicts an end view of one embodiment of a support rod;

FIG. 70 depicts a side view of the support rod of FIG. 69;

FIGS. 71-74 depicts various views of different configurations of one embodiment of a multiple transverse connector system, shown in a single construct;

FIG. 75 depicts an exploded side view of one embodiment of a screw driver assembly;

FIG. 76 depicts a partially-exploded side view of the screw driver assembly of FIG. 75 and a pedicle screw sub-assembly;

FIGS. 77 and 78 depict various planar views of the screw driver assembly of FIG. 75 and a pedicle screw sub-assembly;

FIG. 79 depicts an enlarged partial view of circle L of the screw driver assembly tip of FIG. 76;

FIG. 80 depicts an enlarged cross-sectional view of the pedicle screw subassembly of FIG. 77 taken along line M-M;

FIG. 81 depicts an enlarged cross-sectional view along line N-N of the pedicle screw subassembly of FIG. 77;

FIG. 82 depicts an enlarged cross-sectional view of the pedicle screw subassembly FIG. 78 taken along line Q-Q;

FIG. 83 depicts an enlarged broken cross-sectional view of circle S of the pedicle screw subassembly of FIG. 78;

FIG. 84 depicts a sectional view the hook pedicle screw system of FIG. 85 taken along line T-T;

FIGS. 85 and 88 depict planar views of one embodiment of a hook subassembly;

FIGS. 86 and 87 depict planar views of one embodiment of a hook saddle;

FIG. 89 depicts an exploded perspective view of the hook pedicle screw system of FIG. 85;

FIG. 90 depicts an end view of one alternate embodiment of an offset hook;

FIG. 91 depicts a perspective view of the offset hook of FIG. 90;

FIG. 106 depicts a perspective view of another embodiment of a pedicle screw system;

FIG. 107 depicts an exploded perspective view of the pedicle screw system of FIG. 106;

FIG. 108 depicts a side view of the pedicle screw system of FIG. 106;

FIG. 109 depicts a cross-sectional view of the pedicle screw system of FIG. 108 taken along line X-X;

FIG. 110 depicts an enlarged section view of circle Y of the pedicle screw system of FIG. 109;

FIG. 119 depicts a side view of another embodiment of a pivoting hook system;

FIG. 120 depicts a cross-sectional view of the pivoting hook system of FIG. 119 taken along line Z-Z;

FIG. 121 depicts an exploded perspective view of the pivoting hook system of FIG. 119;

FIG. 122 depicts a side view of another embodiment of a pivoting hook system;

FIG. 123 depicts a cross-sectional view of the pivoting hook system of FIG. 122 taken along line AA-AA;

FIG. 124 depicts an exploded perspective view of the pivoting hook system of FIG. 122;

FIG. 125 depicts a side view of another alternative embodiment of a pivoting hook system;

FIG. 126 depicts a cross-sectional view of the pivoting hook system of FIG. 125, taken along line AB-AB;

FIG. 127 depicts an enlarged cross-sectional view of circle AC of the pivoting hook system of FIG. 126;

FIG. 128 depicts an exploded perspective view of the pivoting hook system of FIG. 125;

DETAILED DESCRIPTION OF THE DRAWINGS

Figure 1:
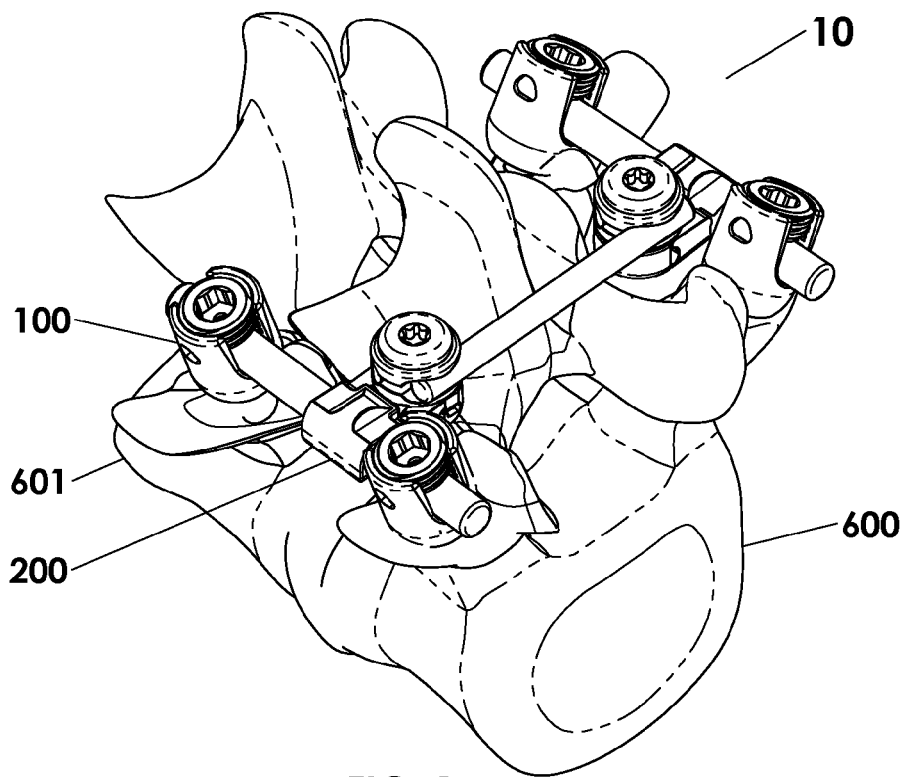
FIG. 1 depicts a front perspective view of one exemplary embodiment of a pedicle screw system 100, shown implanted on a vertebral body segment.

In the following detailed description, for purposes of explanation, numerous specific details are set forth to provide a thorough understanding of the various embodiments of the disclosure. Those of ordinary skill in the art will realize that these various embodiments are illustrative only and are not intended to be limiting in any way. In addition, for clarity purposes, not all of the routine features of the embodiments described herein may be shown or described for every alternative embodiment. One of ordinary skill in the art would readily appreciate that in the development of any such actual implementation, numerous implementation-specific decisions may be required to achieve specific design objectives. These design objectives may vary from one implementation to another and from one developer to another, and the variations thereof are contemplated and included in the present disclosure.

Various of the embodiments described herein include features that facilitate the assembly of surgical constructs, including surgical spinal fusion and/or stabilization constructs, which allow the surgeon the ability to move, reorient and/or otherwise manipulate various adjustable component features, yet maintain the various adjustable components in a desired position and/or orientation and/or connection arrangement while in an unfixed condition (i.e., a "non-tightened" assembly). In addition, various embodiments described herein facilitate the surgeon's assembly and/or adjustment of one or more assembled components within a surgical wound without fear that the components will undesirably separate or otherwise inadvertently disassemble in some manner.

It should be understood that the term "system," when referring to various embodiment described in the present invention, can refer to a set of components which includes multiple bone stabilization components such as superior, cephalad or rostral (towards the head) components configured for implantation into a superior vertebra of a vertebral motion segment and inferior or caudal (towards the feet) components configured for implantation into an inferior vertebra of a vertebral motion segment. A pair of such component sets may include one set of components configured for implantation into and for stabilization of the left side of a vertebral segment and another set configured for the implantation into and for stabilization of the right side of a vertebral segment. Where multiple bone segments such as spinal segments or units are being treated, the term "system" may refer to two or more pairs of component sets, i.e., two or more left sets and/or two or more right sets of components. Such a multilevel system can also involve stacking of component sets in which each set includes a superior component, an inferior component, and one or more medial components therebetween, which may be interconnected and/or independent from each other.

The superior and inferior components (and any medial components therebetween), when operatively implanted, may be engaged or interface with each other in a manner that enables the treated spinal motion segment to mimic the function and movement of a healthy segment, may alter the relative movement of the various spinal structures in a desired manner and/or may simply fuse the segments such as to eliminate pain and/or promote or enhance healing. The interconnecting or interfacing systems can include one or more structures or members that enable, limit and/or otherwise selectively control spinal or other body motion. The structures may perform such functions by exerting various forces on the system components, and by extension on the target vertebrae. The manner of coupling, interfacing, engagement or interconnection between the subject system components may involve compression, distraction, rotation or torsion, or various combinations thereof. In certain embodiments, the extent or degree of these forces or motions between the components may be intraoperatively selected and/or adjusted to address the condition being treated, to accommodate the particular spinal anatomy into which the system is implanted, and to achieve the desired therapeutic result.

Components

In various exemplary embodiments, a spinal fusion system (or other orthopedic construct, including spinal motion and/or dynamic stabilization constructs) may contain various combinations, sizes and configurations of the components described hereafter.

FIG. 1 depicts a front perspective view of one embodiment of a pedicle screw construct 10 incorporating various features of the present invention. The construct 10 includes pedicle screw assemblies 100, which are anchored to vertebral bodies 600 and 601, and a transverse connector 200. The pedicle screw assemblies 100 are placed into the pedicle bone of the vertebral bodies 600 and 601 with the use of various standard surgical instruments through open or minimally invasive surgical approaches. The pedicle screw assemblies 100 typically require a screw driver 300 or other placement device for the initial placement of the bone screw 120 into the bony pedicle. Various embodiments of the present invention include unique features providing a novel interface between the screw driver 300 and the bone screw 120 for desirably providing for secure alignment of the screw into the bone. Also shown in embodiment 10 is a transverse connector assembly 200 (see also FIG. 32) that desirably provides additional rigidity for the construct, which may be especially useful in spinal fusion procedures where larger constructs (typically of longer lengths where multiple vertebral bodies and/or levels are fused) or if a vertebral body is "skipped" between fixation levels (i.e., the intermediate vertebral level does not contain a pedicle screw assembly) because of surgeon choice. It is known to those familiar in the art of spinal fusion that a transverse connector assembly is not always required during a fusion procedure, so the fusion construct might only contain as few as two pedicle screw assemblies 100 and one support rod 150.

For simpler description purposes FIGS. 2-6 and 9-31 will describe various exemplary components, and interfacing of components in a variety of ways, of embodiments of a pedicle screw assembly 100 constructed in accordance with various teaching of this invention. As best seen in FIG. 3, an exploded perspective view of the pedicle screw assembly 100 reveals a tulip body 110 (also referred to as a coupling device, head, seat or anchor), a bone screw 120 (or various other types of fixation elements), a lower saddle 130 (also referred to as an insert), a support or connecting rod 150 and a cap or set screw 140.

Figure 100:
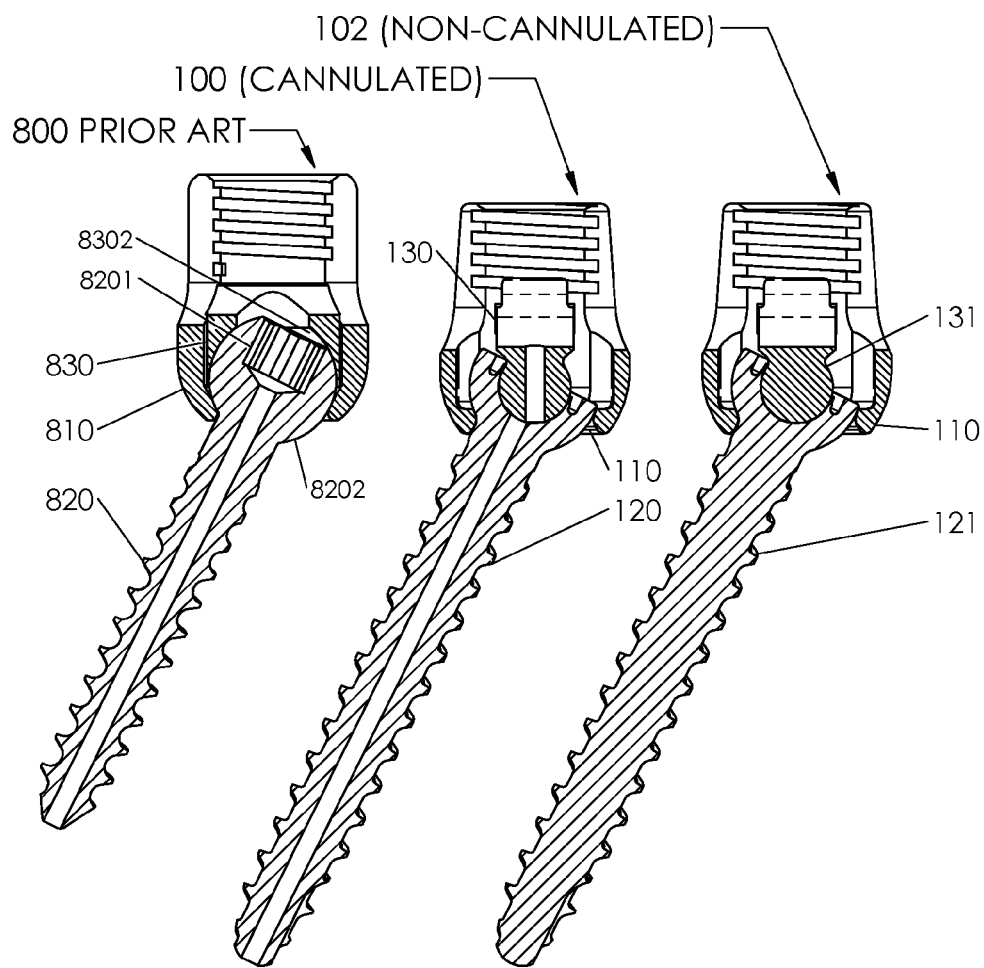
FIG. 100 depicts enlarged cross-sectional views of the prior art, cannulated and non-cannulated pedicle screw subassemblies of FIG. 99, taken along line V-V.

The bone screw 120 (see FIGS. 12-16) can include a variety of features similar to those of prior art screws (see FIGS. 7-8), including the incorporation of screw threads 1209 and/or a generally symmetrical outer spherical radius 1201, which are similar to screw thread 8203 and outer spherical radius 8202 of prior art screws. In various embodiments, a bone screw cannulation 1205 can be provided, which can include a hole through the entire length of the screw, which might be used in specific surgeries where the screw is desirably guided along a guide wire (not shown) that travels through the pedicle screw sub-assembly 101, and which might also incorporate a lower saddle cannulation 1307 (see FIG. 27), if desired. It is well known in the field of spinal surgery that components 120 and 130 can also have no cannulation (i.e., are solid in the center—see non-cannulated screw 121 and non-cannulated lower saddle 131 in FIG. 100). If desired, the bone screw 120 can also contain a single self-tapping notch or "tooth" and/or multiple self-tapping notches 1210 (see FIG. 16) to ease the insertion of the bone screw into a vertebral body. Bone screws can be manufactured in various lengths, diameters, thread pitches and thread forms, and since these details are generally not considered unique to this invention on their individual bases, they will not be further described individually herein.

Figure 10:
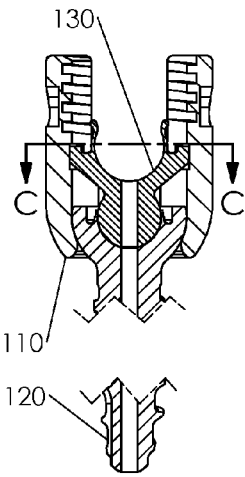
FIG. 10 depicts an end cross-sectional view along line B-B of the pedicle screw subassembly of FIG. 9.

One unique feature of the bone screw of the present invention includes various features incorporated into the head of the bone screw 120, which can include a male outer spherical radius 1201 (see FIG. 14) and a female inner spherical radius 1202, that can be formed concentric to each other. On the end of the female inner spherical radius 1202 can be disposed one or more thin tabs 1203, which as shown diverge below the female inner spherical radius 1202 (which in various embodiments may include opposing tabs that converge towards each other and/or one or more non-symmetrical tabs biased towards the central longitudinal axis of the screw) and are desirably formed such that at least one of the thin tabs 1203 have the capacity to "flex" or deflect to some degree, desirably causing one or more of the thin tabs 1203 to have a retaining function and/or provide a "friction fit" with a corresponding male spherical radius 1301 of the lower saddle 130 (see FIGS. 10 and 24). In the disclosed embodiment, the thin tabs 1203 are separated by slots 1208, and while the figures show six slots 1208 and six tabs 1203, a variety of numbers of tabs and slots and tab/slot spacing/orientation (i.e. regularly or irregularly spaced, opposed pairs and/or oddly-spaced tabs or slots such as three equal tabs) may be used and still be within the scope of this invention. Also shown is a circular channel 1204 (see FIG. 14) which can be incorporated into the design to desirably allow a greater amount of free flexible movement of, or clearance for, the thin tabs 1203 when the lower saddle 130 is placed into the bone screw 120 and tulip body 110 of the sub-assembly 101, such as shown in FIG. 10.

Another unique feature of the present invention includes various driving features disclosed in various exemplary embodiments described herein, such as driving features 1206 and 1207 (see FIG. 15) disposed on the spherical end of the bone screw 120. In a prior art bone screw (see FIG. 8) the bone screw is typically driven by a relatively small diameter female hex or hexalobe 8201 (which can include a socket arrangement commonly referred to as a TORX™ socket and driver, which is commercially available from Camcar Textron of Providence, R.I., USA). The size of the driver and socket in these types of arrangements are generally substantially smaller than the outer diameter of the screw head, as the outer walls of the socket must be sufficiently thick to withstand the rotational torque of the driver, and the size limits of the spherical radius 8202 must be sufficient to accommodate both the socket and the surrounding wall thickness. In hard bone of the vertebra 600, the small diameter of the female hexalobe 8201 or the mating tip of the prior art screw driver can strip or even fracture. Moreover, the form of a hex or hexalobe does not provide significant direct driving forces between the male driver and female driving features of the screw, but rather primarily relies upon angular contact regions, which can result in significantly greater stresses on the system. In contrast, the driving arrangements described in the various embodiments of the present invention enables the user to impart forces on both large indirect driving faces 1207 and large direct driving faces 1206 (see FIG. 15) for insertion or removal of the bone screw. The faces 1206 and 1207 desirably mate with the corresponding faces 3102 and 3104 on the bifurcated tangs 3105 of the screw driver 300 respectively (see FIGS. 79 and 80).

Figure 14:
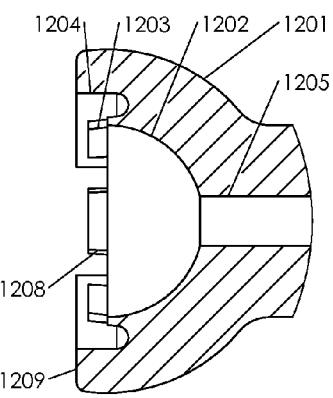
FIG. 14 depicts a magnified partial side view of circle F of the pedicle screw of FIG. 13.
Figure 13:
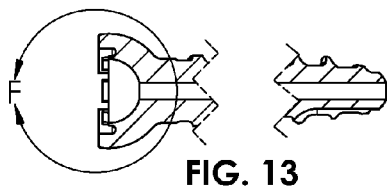
FIG. 13 depicts a broken side cross-sectional view along line D-D of the pedicle screw of FIG. 12.
Figure 15:
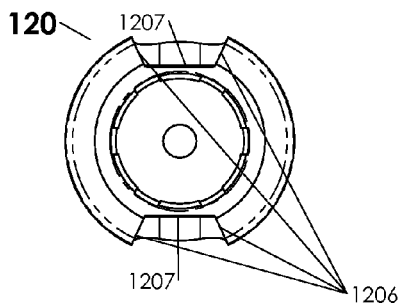
FIG. 15 depicts a top view of the pedicle screw of FIG. 12 taken along line E-E.
Figure 16:
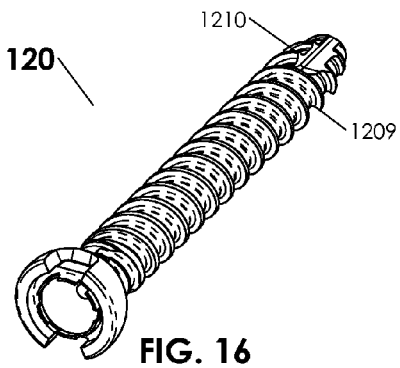
FIG. 16 depicts a top perspective view of the pedicle screw of FIG. 12.
Figure 17:
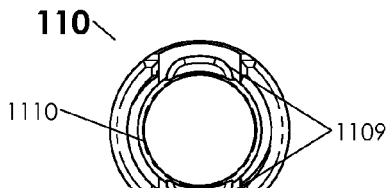
FIG. 17 depicts a top view of one embodiment of a tulip body.

When a screw driver 300 is inserted into the pedicle screw sub-assembly 101, the bifurcated tangs 3105 can travel into the clearance pockets 1109 of the tulip body (see FIGS. 17, 21, 80, 81 and 83) and the faces 3103 on the bifurcated tangs 3105 (see FIGS. 79 and 83) desirably come into contact with the planar face 1209 of the bone screw 120 (see FIGS. 14 and 83). Once this contact is made the male thread 3302 of the sleeve 330 of the screw driver 300 can be threaded into the female threads 1104 of the tulip body (see FIG. 82). As the sleeve 330 is rotated around the shaft 310 of the screw driver 300, the planar face 3301 of the sleeve 330 (see FIG. 79) will come into contact with the planar faces 3101 of the shaft 310 (see FIG. 81). Once contact between the two planar faces 3101 and 3301 is accomplished, further rotation of the sleeve 330 will desirably draw the pedicle screw assembly in the direction of the arrow (shown in FIG. 83) until the whole assembly of the pedicle screw sub-assembly 101 and the screw driver 300 are desirably locked together as one rigid assembly, making it very easy for the surgeon to insert the bone screw 110 into the vertebral body without the sub-assembly 101 falling off of the screw driver 300. Because the components are now rigidly locked together at the planar faces 1209 and 3103 (see FIG. 83), the bone screw 120 will desirably not tip or angle away from the centerline axis of the screw driver 300.

In FIGS. 4-6 it can be seen how the tulip body 110 or housing, with its attached components lower saddle 130, support rod 150 and set screw 140, can desirably be rotated to various conical angles around concentric spherical radii 1201 and 1202 of the bone screw 120, tulip body spherical radius 1101 and spherical radius 1301 of the insert, prior to final tightening of the pedicle screw assembly 100. In various embodiments, a friction fit between the thin tabs 1203 and the male spherical radius 1301 of the lower saddle 130 is desirably created by the positioning, dimensioning and tolerancing of the tabs and/or radius relative to each other such that this interaction does not allow the tulip body to "flop around loosely" during surgery (prior to final tightening of the screw construct) and thereby provide a relatively stable construct (which can be readily moved by the surgeon, if desired) while the surgeon is placing the support rod 150 and set screw 140 into the pedicle screw sub-assembly 101.

Figure 95:
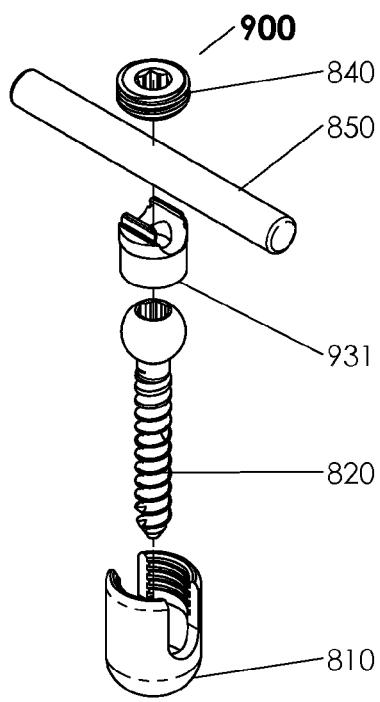
FIG. 95 depicts an exploded perspective view of another embodiment of a pedicle screw system.
Figure 96:
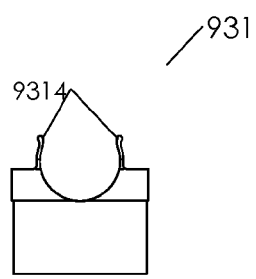
FIGS. 96 and 97 depict various views of an alternate embodiment of a lower saddle.
Figure 97:
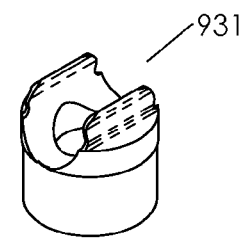
Figure 98:
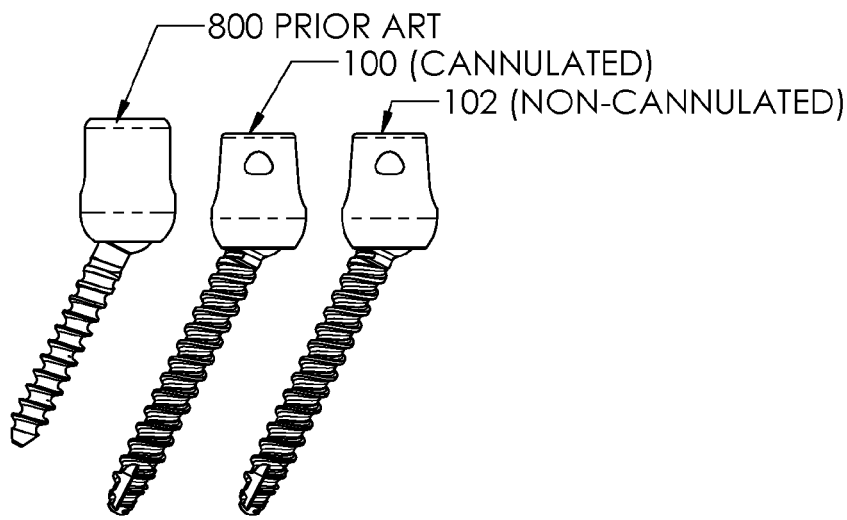
FIG. 98 depicts side views of one embodiment of a prior art pedicle screw subassembly, one embodiment of a cannulated pedicle screw subassembly and one embodiment of a non-cannulated pedicle screw subassembly.
Figure 99:
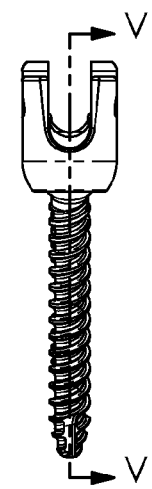
FIG. 99 depicts an end view of the subassemblies of FIG. 98.

Also shown in the cross sectional view of FIG. 6 are the placements of the various components of the pedicle screw assembly 100 in this embodiment, and how these components interface with each other. Since the spherical radii 1101, 1201, 1202 and 1301 can be formed concentrically, they form an articulating poly-axial construct. The flexible fingers 1304 of the lower saddle 130 (see FIG. 24) can dimensioned, tolerance, engineered and/or manufactured in a size and shape to "squeeze" the support rod 150 and retain the rod when it is placed into the sub-assembly 101. In various embodiments, the flexible fingers 1304 will desirably provide an audible and/or tactile feedback to the surgeon when the support rod 150 "snaps" into the lower saddle rod diameter 1302 from spring pressure of the flexible fingers 1304. Once the support rod 150 is inserted into the lower saddle 130, frictional forces (at least in part due to the presence and/or pressure of the flexible fingers 1304) keep the rod from slipping and/or significantly moving in the lower rod diameter 1302. However, the spacing and/or pressure between the flexible fingers 1304 desirably allows the surgeon to easily slide and/or otherwise move the support rod to an optimal and/or desired position. Those skilled in the art would comprehend that such a unique retention feature of the invention could be accomplished using a variety of alternative shapes and/or sizes of retention members, as well as various forms of lower saddles. In various additional embodiments, the retention features described herein may be incorporated into prior art designs, creating designs such as shown in FIGS. 95-97, where another exemplary embodiment 900 of the present invention is depicted with a lower saddle or insert 931 incorporating flexible fingers 9314 (see FIG. 96) or in alternative embodiment the flexible fingers could possibly be removed from the lower saddle 130 and added (in an embodiment not shown) directly to the tulip body 110.

Figure 21:
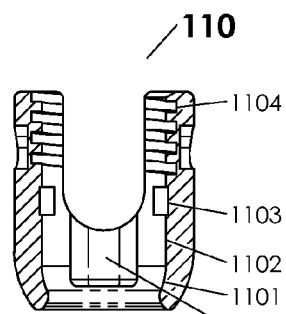
FIG. 21 depicts a side cross-sectional view of the tulip body of FIG. 18 taken along line G-G.
Figure 20:
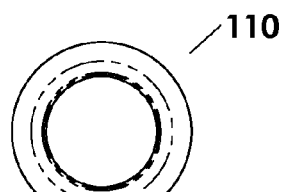
FIG. 20 depicts a bottom view of the tulip body of FIG. 17.
Figure 23:
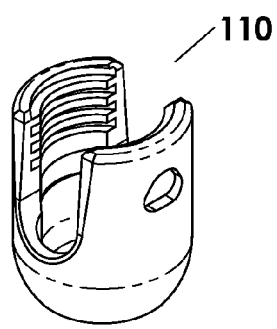
FIG. 23 depicts a perspective view of the tulip body of FIG. 17.

Once the pedicle screw sub-assembly 101 and support rod 150 are in a desired position and/or orientation, the surgeon can then thread (see FIG. 6) the male thread 1404 of the set screw 140 (see FIG. 30) into the mating female threads 1104 of the tulip body (see FIG. 21). When the planar face 1401 of the set screw 140 (see FIG. 31) comes into contact with the support rod diameter 1501 (see FIG. 69) the pedicle screw assembly 100 becomes a complete subassembly. When the surgeon has completed all the placements of pedicle screw subassemblies 100 and support rods 150, the surgeon can then perform a final tightening sequence of the set screws 140, using the female hex 1402 with an appropriate hex screw driver to a final pre-determined torque value. Those skilled in the art should appreciate that the female hex 1402 arrangement described herein, along with the set screw 140, could be formed in various alternative shapes, such as a hexalobe (Torx), a square, a slotted, a cross or other shapes.

Various prior art components, including simplified versions of screw components depicted in patents by Sherman (U.S. Pat. No. 5,879,350), Farris (U.S. Pat. No. 6,485,491), Biedermann (U.S. Pat. No. 6,835,196), Jeon (U.S. Pat. No. 6,905,500 and Konieczynski (U.S. Pat. No. 7,087,057) are shown in FIGS. 7, 8, 92, 93 and 94, which are utilized as comparisons to demonstrate various unique features of the various embodiments of the present invention. The prior art pedicle screw assemblies include many similar component parts, however the specific design and/or features of many of these components differs significantly from the features of many embodiments described herein, which can include (but are not limited to) unique screw driving features 1206 and 1207, thin tabs 1203 and lower saddle flexible fingers 1304 (as described in various locations of the description herein). Those of ordinary skill in the art will understand that the flexible 1304 fingers of the lower saddle (or other features) might alternatively be designed integrally into an embodiment of the tulip body or housing, and thus not be directly attached to the lower saddle insert 130.

Figure 11:
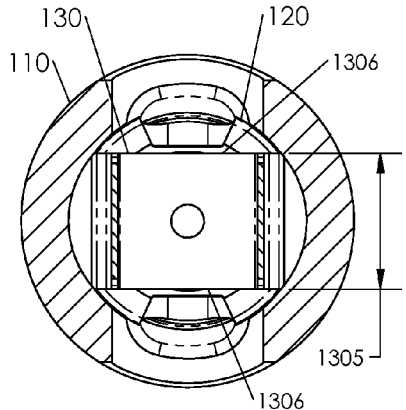
FIG. 11 depicts a magnified top cross-sectional view along line C-C of the pedicle screw subassembly of FIG. 10.
Figure 12:
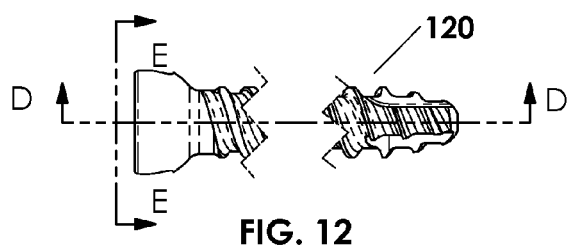
FIG. 12 depicts a broken side view of one embodiment of a pedicle screw.

FIG. 11 is a sectioned view along line C-C of FIG. 10 which depicts a portion of the top of the bone screw 120 along with sections of the lower saddle 130 and tulip body 110. Also seen in this sectioned view are the planar surfaces 1306, which are formed in this embodiment to be a predetermined distance apart 1305 that is desirably less than the inner diameter of the tulip body 110, thereby allowing for sufficient clearance for the tangs 3105 of the driver 300 to contact the bone screw 120.

Figure 18:
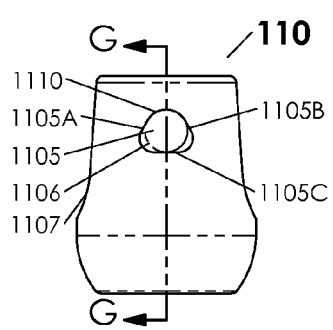
FIGS. 18 and 19 depict various side views of the tulip body of FIG. 17.
Figure 19:
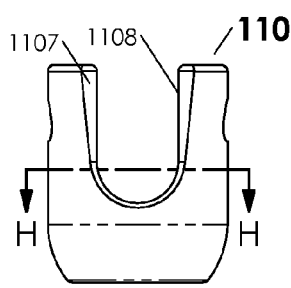
Figure 22:
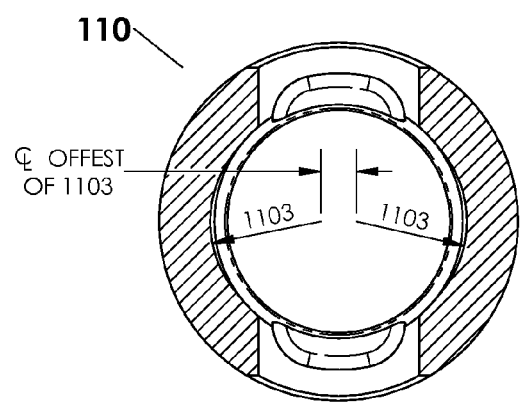
FIG. 22 depicts a magnified top cross-sectional view of the tulip body of FIG. 19 taken along line H-H.
Figure 101:
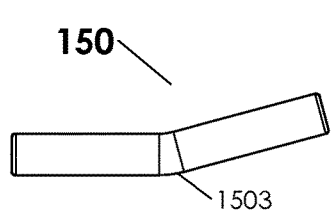
FIG. 101 depicts a side view of one embodiment of a bent support rod.
Figure 102:
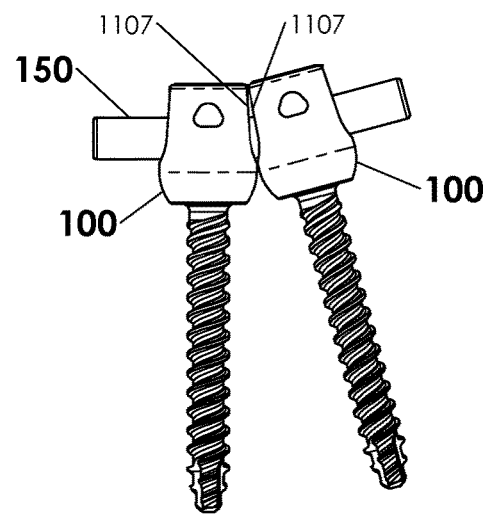
FIG. 102 depicts a side view of two adjacent pedicle screw subassemblies attached to the bent support rod of FIG. 101.

In FIGS. 17-21, various planar views of the tulip body 110 show other features of this invention. One or more clearance surfaces 1107 (which may be symmetrical and/or nonsymmetrical—see FIGS. 18 and 19) can be designed to allow closer placement of adjacent bone screw sub-assemblies 100 (see FIG. 102), especially where the use of an angular support rod is contemplated and/or desired, such as when using a support rod 150 that includes a bent area 1503 (see FIG. 101). In FIG. 21, where a section view along line G-G of FIG. 18 is depicted, the two symmetrical lower saddle radial pockets 1103 are shown and also are shown in the enlarged section view of FIG. 22. In the disclosed embodiment, the lower saddle radial pockets 1103 are not necessarily concentric, as their centerlines can be offset (as shown in FIG. 22) and they desirably mate with the symmetrical radial surfaces 1303 of the lower saddle 130, desirably having centerlines that are also offset with each other (see FIGS. 24 and 27). These non-concentric mating surfaces 1103 and 1303 can be designed in this manner so as to inhibit and/or prevent rotation when assembled together as shown in FIG. 11. FIG. 18 depicts symmetrical attachment pockets 1105 on each side of the tulip body 110. These attachment pockets 1105 are triangular in shape (although other shapes could function in a similar manner) to allow a mating male triangular tab (not shown) to lock onto the tulip body 110 and manipulate it into the desired position by the surgeon. Designed into the attachment pockets 1105 is an upper radius 1110 that has a clearance diameter 1106 which can accept an instrument with mating male round tabs which will desirably not immovably lock onto the tulip body 110 because the triangular planar surfaces 1105A, 1105B and 1105C are not necessarily engaged with the instrument, but may rather allow the surgeon to use the upper radius 1110 as a pivot point for a fulcrum or attachment of various other instruments to assist with the physician's manipulating the position of the construct.

FIGS. 28-31 depict perspective and planar views of one exemplary set screw 140 which shows a thread (which may be an industry standard square buttress thread or other thread form, if desired). The set screw 140 has a planar surface 1401 that desirably contacts the rod diameter 1501 of the support rod 150 when assembled (see FIGS. 6 and 69). When the set screw 140 is threaded to a specific torque value in the tulip body, the various components of the sub-assembly 100 (see FIG. 6) desirably become locked together. Also shown in these figures is an optional through diameter 1403, which can be used in conjunction with a guide instrument to slide the set screw 140 into position. Those of ordinary skill in the art should understand that the set screw 140 can also be manufactured without the diameter 1403, without impeding the function of the planar surface 1401.

FIGS. 106-110 depict various views of one alternative embodiment of a pedicle screw system, in which a lower saddle 132 includes a plurality of connecting or "provisional attachment and/or connection" elements that attach the lower saddle or insert 132 to the tulip body 132, to the rod 150, and to the bone screw 122. Desirably, these various connecting provisional attachment elements connect various components of the pedicle screw system to inhibit and/or prevent disassembly of the connected components, yet allow some relative movement between the connected components. Moreover, the provisional attachment elements desirably provide various clamping, resisting and/or frictional forces to inhibit and/or prevent undesirable movement between the connected components, such as "floppiness" and/or unwanted movement of the components prior to securing on the targeted bone segment and/or prior to final tightening of the construct, yet allow the physician the ability to manipulate, move and/or reorient the various attached components (relative to each other) by applying some nominal amount of external force. Desirably, the provisional attachment elements will not interfere with the final fixation and tightening of the pedicle screw components, which can desirably create a rigid construct and/or subcomponent, as desired.

Figure 111:
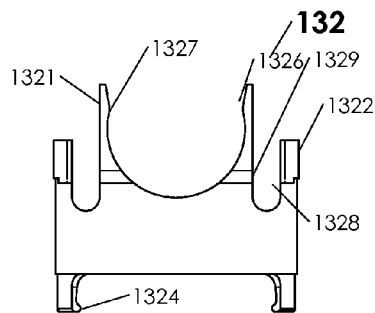
FIGS. 111 through 113 depict various views of an alternate embodiment of a lower saddle.
Figure 112:
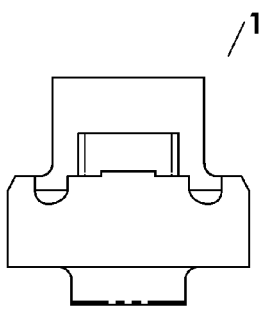
Figure 113:
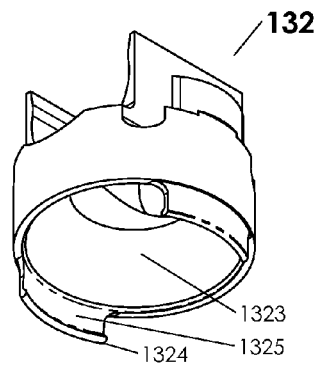

As best seen in FIGS. 111 through 113, the lower saddle or insert 132 can include various "provisional" or "temporary" attachment elements such as flexible fingers 1321 and/or thin spring arms 1325. In the disclosed exemplary embodiment, the lower saddle 132 can include at least one flexible finger 1321 extending upward from the lower saddle body (in the disclosed embodiment, two such fingers are shown). The flexible fingers 1321 may include an outer surface 1329, an inner rod seat surface 1326 and optional retention tabs 1327. The flexible fingers 1321 can be desirably spaced apart to form a channel or opening 1326 that is sized to fit a support rod 150. The support rod 150 can be inserted in the channel or opening 1326 and positioned in the inner rod seat surface 1326. In the disclosed embodiment, the inner surface of the flexible fingers include optional extensions or retention tabs 1327, which desirably project inward from the flexible fingers into the inner channel 1326, where the spacing between the retention tabs is desirably smaller than an outer diameter of the support rod 150. When the support rod 150 is first inserted into the opening or channel 1326, the rod will contact the retention tabs 1327, and additional pressure on the rod from the surgeon's hand (with continued insertion of the rod) will desirably flex or bend outward the flexible fingers 1321 to some extent, with the rod sliding past the retention tabs 1327. Once the support rod 150 passes the retention tabs, the fingers will desirably slide or "snap" back towards their original position, with the rod fully seating into the opening or channel 1326 and the flexible fingers 1321 desirably returning at or near their original positions. Once the rod is in a desired position within the channel 1326, the flexible fingers 1321 can (if desired) place a compressive force on the outer surface of the support rod 150 (to desirably inhibit and/or control movement of the rod along its longitudinal axis), and the retention tabs 1327 and associated flexible fingers 1321 will desirably retain the support rod 150 within the channel 1326. Desirably, this arrangement will serve to "hold" the rod with sufficient force to inhibit uncontrolled longitudinal movement relative to the lower saddle 132, yet allow longitudinal movement of the rod relative to the lower saddle 132 and/or housing upon urging from the physician.

Figure 114:
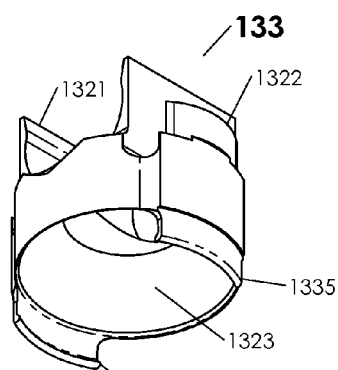
FIGS. 114 through 116 depict various views of another embodiment of a lower saddle.

In various embodiments depicted herein, the lower saddle 132 will desirably fit into and be secured within the tulip body or housing 112. As best seen in FIGS. 110 and 114, the lower saddle 132 can include one or more flexible tabs 1322 on an outer surface, which can desirably fit into corresponding lower saddle radial pockets 1122 (see FIGS. 21 and 22) of the tulip body 112. Alternatively, the one or more flexible tabs 1322 (and/or some or all of the outer surface of the lower saddle body, if desired) could frictionally fit and/or "wedge" against one or more inner surfaces of the tulip body 112, if desired. In various alternative embodiment, the flexible tabs 1322 and/or lower saddle pockets 1103 could include one or more flat or planar surfaces which interact, "snap" and/or otherwise lock when the lower saddle 132 has been rotated into a desired position within the tulip body 112. In various other embodiments, the flexible tabs 1322 and/or lower saddle pockets 1103 could include surface features (i.e., patterns and/or surface roughness) on one of more interacting surfaces to increase frictional attachment to the tulip body 112.

In various embodiment, the flexible tabs 1322 are desirably spaced apart from the flexible fingers 1329, with a gap or opening 1328 between the flexible fingers 1329 and flexible tabs 1322 which desirably allows the independent flexing and/or compression of either or both of the flexible fingers 1321 and/or the flexible tabs 1322. In one exemplary embodiment, the gap or opening 1328 may not extend as deep or as wide as depicted in FIG. 111, which may result in some restriction in the flexion and/or compression of the flexible fingers 1321 and/or flexible tabs 1322, while in others the gap 1328 may equal the depth of the channel 1326 (see FIG. 111) or may exceed the depth of channel 1326.

In various embodiments, the lower saddle 132 may be designed with one or more (i.e., at least two, in the various disclosed embodiments) spring arms 1325 on a lower portion, such as shown in FIGS. 110 and 113, which desirably extends at least partially around a circumference of the bone screw and "grips" the male spherical diameter 1221 of the bone screw, desirably retaining the head of the bone screw and also creating some level of compression force and/or frictional resistance between the lower saddle 132 and the head of the bone screw 122. In various embodiments, the thin spring arms 1325 of the lower saddle 132 can form a portion of a female spherical diameter 1323 formed on a lower portion of the lower saddle 132, with the male spherical diameter 1221 of the bone screw 122 being moveably secured within the female spherical diameter 1323, where frictional forces and/or tension forces of interacting friction surfaces 1324 contacting the spherical diameter 1221 of the bone screw 122 creates a resistance that desirably inhibits completely free movement of the bone screw 122 relative to the lower saddle 132, yet allows relative movement between the bone screw and the lower saddle when induced by sufficient force from the surgeon. The spring arms 1325 (as shown in FIG. 113) and/or other areas of the lower saddle 132 may be designed to include various channels or openings with an equivalent and/or smaller dimension than the spherical diameter 1221 of the bone screw 122, which could allow for deflection of the thin spring arms 1325 such that they could pass over the larger spherical diameter 1221 of the bone screw 122 with little or no resistance, yet allow sufficient frictional resistance forces to accomplish the various objectives of the present invention. The thin spring frictional arms 1324 may include an additional frictional projecting lip 1324 (see FIG. 114) that can extend perpendicular and/or outwardly from the surface of the thin spring arms 1324 that could optionally provide additional clamping force onto the spherical diameter 1221 of the bone screw 122.

The resulting resistance to relative movement between the lower saddle and the head of the screw desirably prevents the tulip body 112 from "flopping around" relative to the screw head after the screw assembly is inserted into the vertebral body and the insertion tool(s) is removed. This system can allow a surgeon to adjust the orientation, movement and/or angulation of the bone screw 122 relative to the tulip body 112 and have such adjustment maintained in a desired position while the surgeon is anchoring additional bone screws 122 into the targeted bone segment and/or placing additional instrumentation onto the spinal construct.

In one exemplary embodiment, the lower saddle 132 may be retained in the tulip body 111 through the interaction of symmetrical lower saddle radial pockets 1112 and symmetrical radial surfaces 1322 (see FIG. 110) in a manner similar to various ones described earlier for the lower saddle 130 and tulip body 110, with the two symmetrical lower saddle radial pockets 1103 engaging with the corresponding symmetrical radial surfaces 1303 of the lower saddle 130. This embodiment 905 can also incorporate flexible fingers 1321 on an upper surface of the lower saddle 132 to desirably maintain pressure on a support rod 150, in a manner similar to the retention of the bone screw by the flexible fingers 1304 of the lower saddle 130. Various views of the flexible fingers 1321, flexible tabs 1322, female spherical diameter 1323, friction surfaces 1324 and spring area 1325 can be seen in FIGS. 111-113.

In various alternative embodiments, frictional and/or other forces interacting between individual elements may be designed into the system to prevent and/or inhibit the tulip body 111 from flopping around relative to the bone screw (in an uncontrolled and/or partially-controlled manner), with the various resistance forces potentially adjusted by designing different configurations of frictional arms, thin spring arms and/or friction projecting lips (or other similar features). FIG. 114 depicts one alternative embodiment of a lower saddle 133, where the lower saddle 133 may be designed with thin spring recessed arm surfaces 1335 to allow relatively less spring pressure than the spring area 1325 of lower saddle embodiment 132. The thin spring recessed arm surfaces 1335 may be designed to a configuration that mates with spherical diameter 1221 of the bone screw 122 (as shown in FIG. 110). The thin spring recessed arm surfaces 1335 may include an optional frictional projecting lip 1324 for additional frictional forces.

Figure 130:
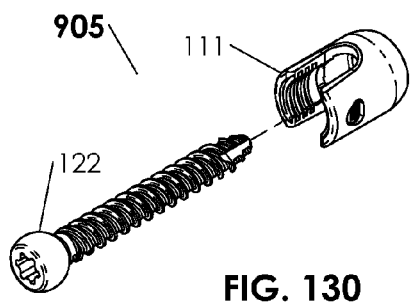
FIGS. 130 through 133 depict exemplary steps for assembling the pedicle screw subassembly of FIG. 107.
Figure 131:
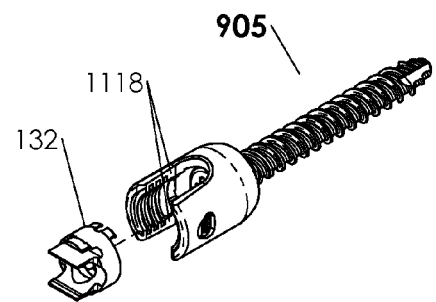
Figure 132:
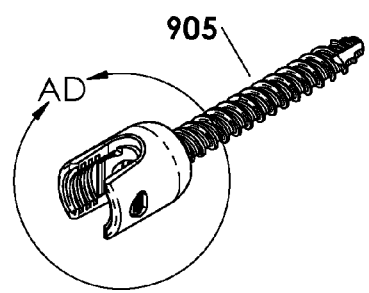
Figure 133:
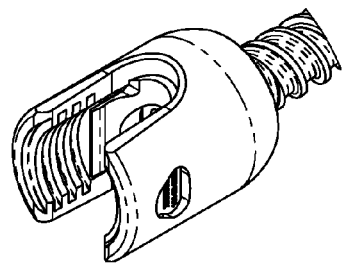
Figure 134:
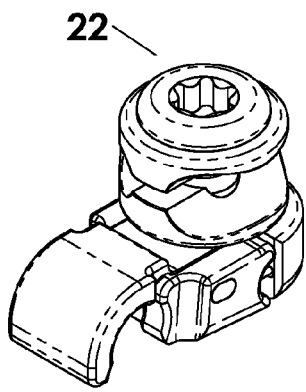
FIG. 134 is a perspective view of an alternative embodiment of a transverse connector.

To initially assemble a pedicle screw subassembly incorporating various lower saddle embodiments (embodiment 905 of FIG. 106 used as an example) with a corresponding tulip body 111, the male spherical head 1221 (see FIG. 107) of a pedicle screw 122 can first be inserted into a female spherical diameter 1111 of the tulip body 111 as shown in FIG. 130. Next the flexible fingers 1321 of the lower saddle 132 are perpendicularly positioned to the symmetrical openings 1118 (see FIG. 131) of the tulip body and inserted into the tulip body 111 till the female spherical radius 1323 of the lower saddle 132 contacts the male spherical 1221 of the pedicle screw 122 as shown in. The lower saddle 132 can then be turned clockwise and/or counterclockwise (i.e., by rotating 90 degrees), thereby inducing the flexible tabs 1322 to deflect inward until the flexible tabs 1322 have mated with the lower saddle radial pockets 1112. A potential audible sound may occur and/or an increase of friction may occur due to a wedging action. The final placement can be seen in FIGS. 132-133. Of course, in alternative embodiments, the securement of the saddle body within the tulip body may be accomplished by wedging the outer surfaces of the lower saddle against the inner surfaces of the tulip body, if desired (which may or may not include locking tabs or other features).

In various alternative embodiments, the pedicle screw 122 and lower saddle 132 may first be assembled (i.e., by insertion of the male spherical head 1221 into the female spherical radius 1323 of the lower saddle 132), followed by insertion and securement of this subassembly into the tulip body 111 (in a manner similar to that previously described).

In various embodiments, the diameter of the pedicle screw head will typically be larger than the diameter of the lower opening 1110 of the tulip body, although in alternative embodiments the pedicle screw head may be equal to or smaller than the diameter of the tulip head lower opening (which could allow for the pedicle screw to be first inserted into the bone, without the attached tulip head and saddle, and then the tulip body and saddle body could be inserted subsequently).

One significant feature of the various embodiments described herein is the ability to "tighten" or immobilize the various elements of the pedicle screw subassembly once the components are in a desired position and/or orientation. Desirably, once a rod has been seated into the lower saddle 132 of an implanted screw assembly, a set screw 140 can be introduced into the tulip body and rotated/tightened. Desirably, advancement of the set screw will push the rod downward into the tulip body, which compresses the insert downward into the tulip body. In turn, the downward movement of the insert sandwiches the head of the pedicle screw between the female spherical diameter 1323 of the insert and an inner surface of the tulip body spherical radius 1101 (see FIG. 6, for example). Desirably, these various compressive forces significantly increase the friction between the various components of the subassembly, effectively immobilizing and/or locking them relative to one another.

In various embodiments, the insert can comprise a variety of materials, but in at least one embodiment the insert comprises an unalloyed or commercially pure Titanium (Ti). This type of material can be particularly useful in orthopedic constructs due to its low biological reactivity. In addition, when used in an insert (such as described herein), the compressive forces induced by rotation of the set screw may be strong enough to induce some portions of the insert material to "flow" or otherwise deform to a limited degree, possibly bonding or "cold welding" various components and significantly increasing the fused strength of the subassembly construct.

Figure 115:
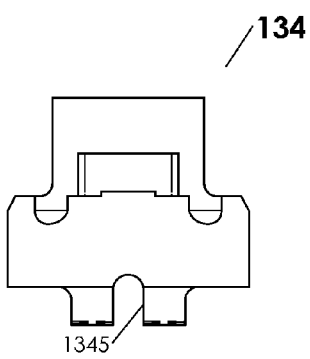
Figure 116:
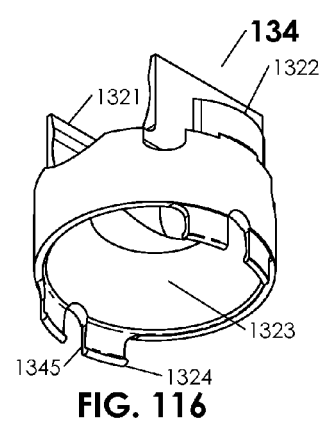
Figure 117:
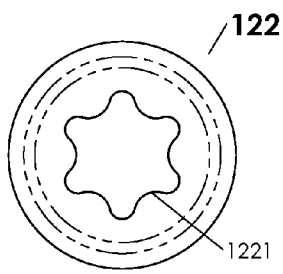
FIG. 117 depicts an end view of an alternate embodiment of a bone screw.
Figure 118:
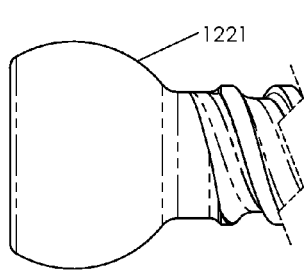
FIG. 118 depicts a broken side view of the bone screw of FIG. 117.

FIGS. 115 and 116 depict an alternative embodiment of a lower saddle 134, where the lower saddle 134 may include slots 1345 to allow less spring pressure (and/or rotation resistance) than the spring area 1325 of lower saddle embodiment 132. The thin spring slotted arms 1335 may include an optional frictional projecting lip 1324 for additional frictional forces. In this embodiment, the flexibility of the spring arms 1345 can be enhanced, even where the spring arms are significantly thicker than those of the embodiment of FIGS. 111-113 or FIG. 114.

Those of ordinary skill in the art should understand that the number of slots 1345, number of friction surfaces 1324 or any combination of recessed surfaces 1335 or non-recessed surfaces, in various combinations, could be possible with varying degrees of effectiveness while significantly retaining the spirit of the present invention. In various alternative embodiments, the thin spring arms on the various lower saddle embodiments described herein might may be designed on opposite sides, adjacent to each other or some angle distanced apart on the circumference of the lower saddle. In additional embodiments, non-symmetrical distributions of spring arms might be utilized.

In various embodiments, a series of pedicle screw subassemblies of different sizes and/or shapes (and associated support rods and/or other components) could be assembled and provided in a kit. A surgeon could then select a desired pedicle screw subassembly, and drive the screw shank into a targeted bony feature using a surgical tool, such as the screw driver having a mating male driving feature that mates with the female driving feature 1221 on the bone screw 122, such as described herein. The surgeon may repeat this approach for additional pedicle screw subassemblies, and then the surgeon could manipulate the tulip heads of one or more subassemblies (as described herein) to align the tulip heads to receive one or more connecting rods. The connecting rod(s) could be placed, and the surgeon could further manipulate the alignment and/or orientation of the various system components. Once in a desired alignment, the surgeon could fixate the various components by placing set screws onto the tulip heads and advancing them in a known manner. If desired, the surgeon may manipulate various component of the surgical construct as desired, without fear of the various untightened components disassembling and/or separating under such manipulation. Once the entire construct is tightened and "locked" in this manner, the surgical wound can be closed and the surgery completed.

Figure 32:
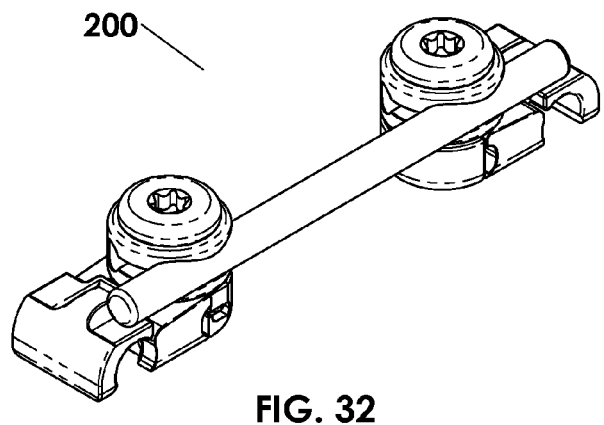
FIG. 32 depicts a perspective view of one embodiment of a transverse connector system.
Figure 33:
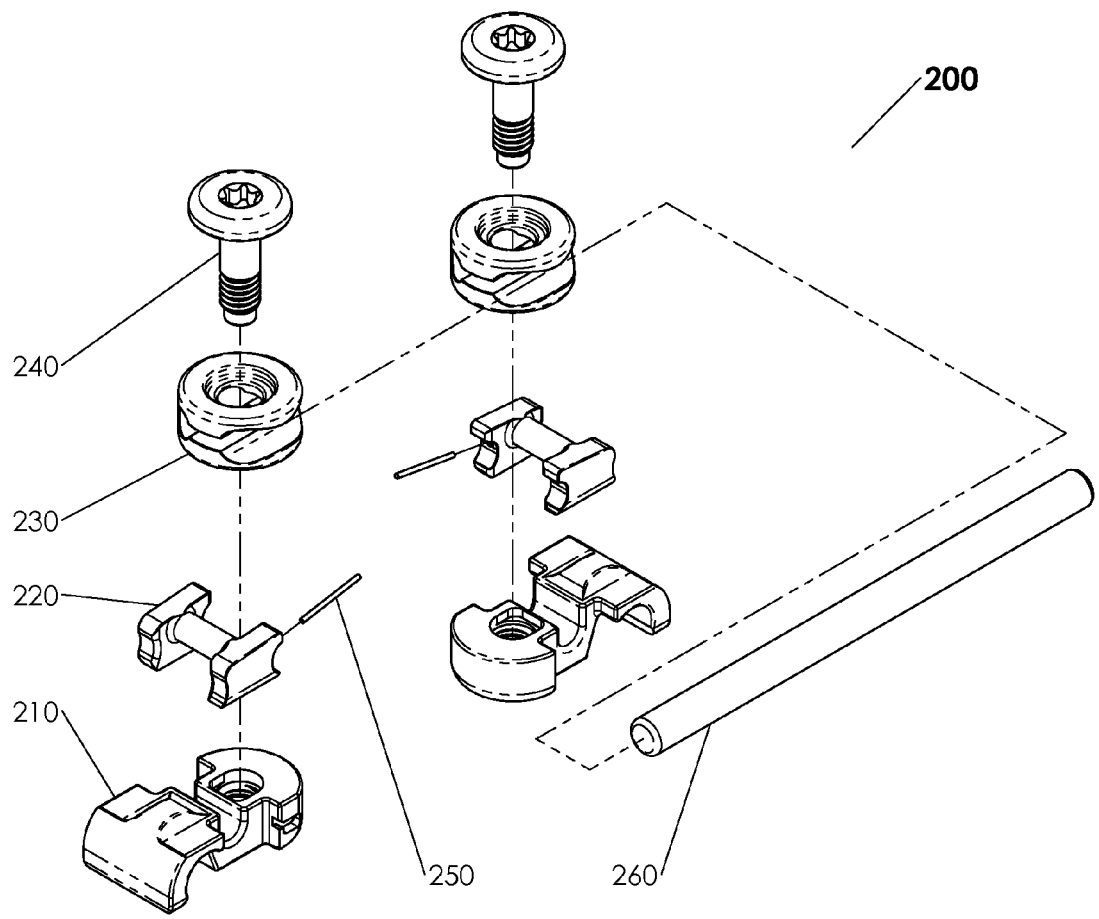
FIG. 33 depicts an exploded perspective view of the transverse connector system of FIG. 32.
Figure 34:
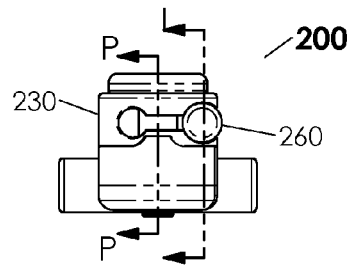
FIGS. 34 and 35 depict various side views of one connector of the transverse connector system of FIG. 32.

FIGS. 32 and 33 depict a perspective and an exploded view of another embodiment of the invention, which is a transverse connector assembly 200. Various types of transverse connectors have been previously connected to pedicle screw constructs, but such subsystems have been loose fitting and cumbersome to put into place. In the exploded view of the transverse connector 200 assembly the following components are included: connector bodies 210, pivot clamps 220, rod clamps 230, clamp screws 240, spring shafts 250 and a connector rod 260.

Figure 60:
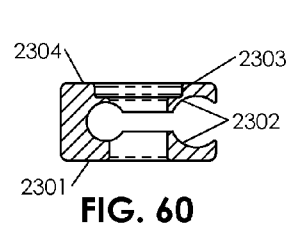
FIG. 60 depicts a cross-sectional view along line W-W of the rod clamp of FIG. 56.
Figure 57:
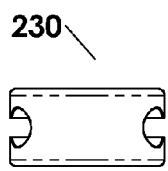
Figure 58:
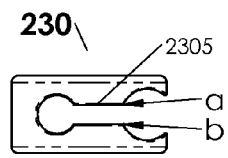
Figure 59:
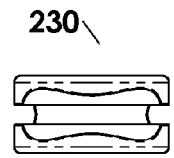
Figure 61:
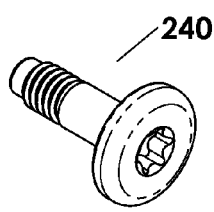
FIG. 61 depicts a perspective view of one embodiment of a clamp screw.
Figure 67:
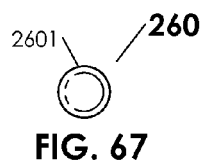
FIG. 67 depicts an end view of one embodiment of a connector rod.
Figure 68:
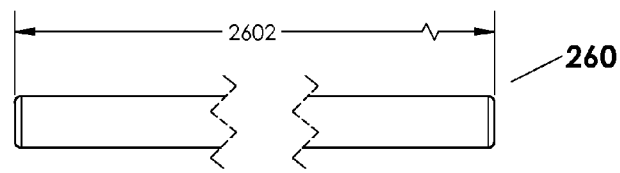
FIG. 68 depicts a broken side view of the connector rod of FIG. 67.
Figure 92:
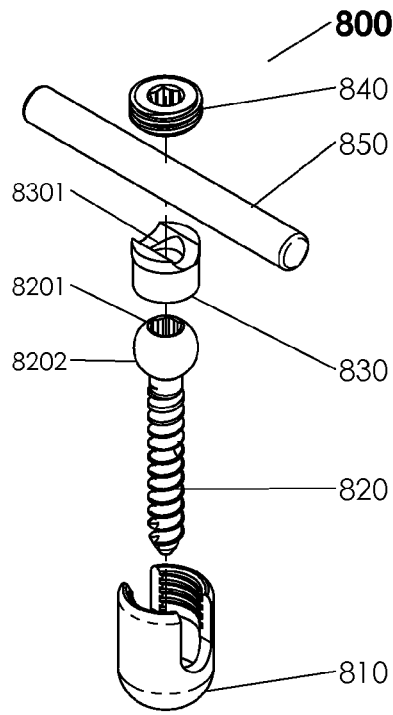
FIG. 92 depicts an exploded perspective view of a prior art pedicle screw system.
Figure 93:
FIGS. 93 and 94 depict various views of one embodiment of a prior art insert.
Figure 94:
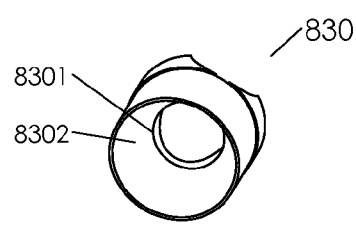

Once various pedicle screw assemblies 100 and support rods 150 have been placed in the bone of the targeted vertebra, a connecting rod 260 of an appropriate length to span two or more support rods can be chosen (see FIGS. 1 and 71). Referring to FIGS. 34-41, two transverse connector sub-assemblies 201 (see FIGS. 38-39) can be placed on the ends of the connecting rod 260. The fit between the connecting rod diameter 2601 (see FIG. 67) of the connecting rod 260 and the connecting rod apertures 2302 (see FIG. 60) of the rod clamp 230 can be a spring or friction fit created by channel 2305, between points a and b (see FIG. 58), that allows the rod clamp 230 to be pushed onto and/or "snapped" over the connecting rod 260 (i.e., using finger pressure) yet remain secure enough on the rod to not allow the transverse connector sub-assemblies 201 to freely rotate and/or move (i.e., under their own weight) from their desired position once in place on the connecting rod 260.

Figure 39:
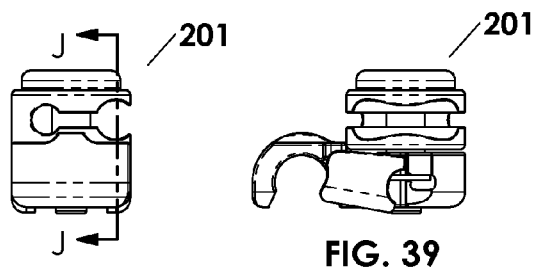
Figure 40:
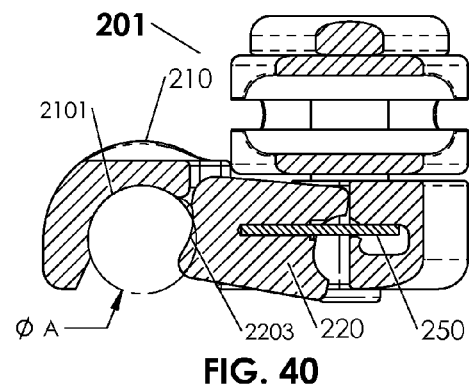
FIG. 40 depicts an enlarged section view of the transverse connector subassembly of FIG. 38 taken along line J-J.
Figure 41:
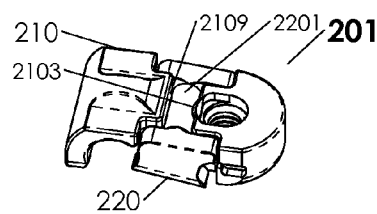
FIG. 41 depicts an isometric view of a portion of the transverse connector assembly of FIG. 34.
Figure 42:
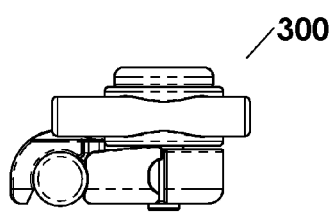
FIG. 42 depicts a side view of an alternative embodiment of a transverse connector system without a spring shaft.
Figure 44:
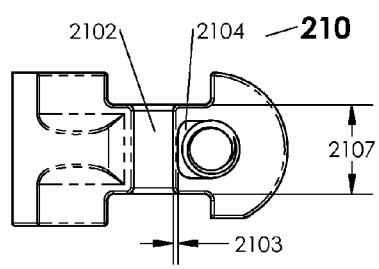
FIGS. 44-48 depict various planar views of the connector body of FIG. 43.
Figure 45:
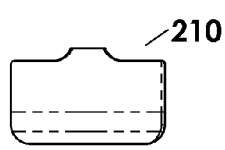
Figure 46:
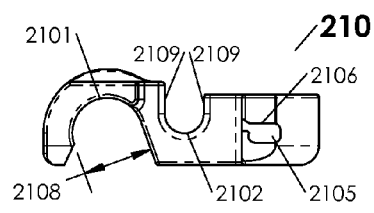
Figure 47:
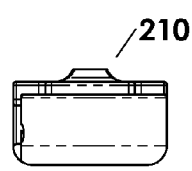
Figure 48:
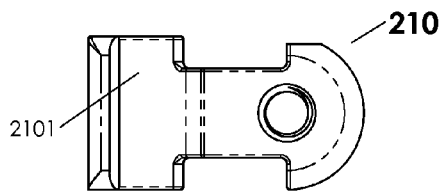
Figure 49:
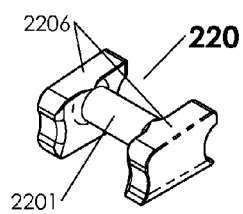
FIG. 49 depicts a perspective view of one embodiment of a pivot clamp.
Figure 50:
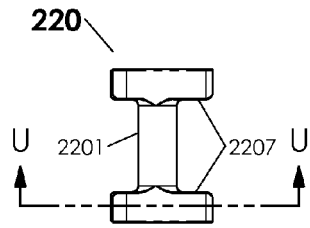
FIGS. 50-53 depict various planar views of the pivot clamp of FIG. 49.
Figure 54:
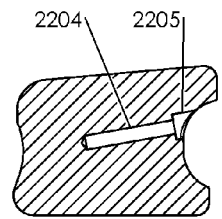
FIG. 54 depicts an enlarged cross-sectional view of the pivot clamp of FIG. 50 taken along line U-U.
Figure 51:
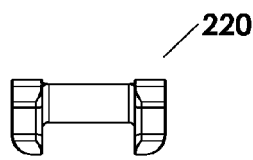
Figure 52:
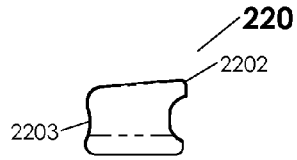
Figure 53:
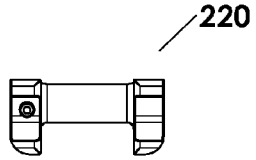
Figure 55:
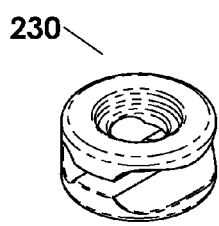
FIG. 55 depicts a perspective view of one embodiment of a rod clamp.
Figure 56:
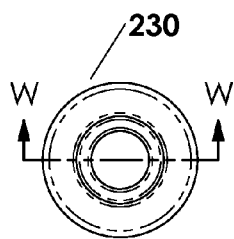
FIGS. 56-59 depict various planar views of the rod clamp of FIG. 55.

In the disclosed embodiment, before the transverse connector assembly 200 is placed onto the support rods 150, the spring shaft 250, which can comprise a flexible super-elastic shape memory metal or other flexible material, is in a straight or unrestrained condition, such as shown in FIGS. 39 and 40. When it is in this position, the rod clamp radius 2203 of the pivot clamp 220 (see FIG. 52) can violate, or swivel past the circle, shown as OA in FIG. 40. The pivot diameter 2201 of pivot clamp 220 (see FIG. 49) rotates in the pivot channel 2102 (see FIGS. 44 and 46) of the connector body 210 while the flanges 2206 (see FIG. 49) on each end of the pivot diameter 2201 are restrained axially by the planar surfaces 2207 of the pivot clamp 220 (see FIG. 50) and the planar walls 2107 (see FIG. 44) of the connector body 210. On the connector body 210 there can be included two tangent walls 2109 in the pivot channel 2101, adjacent to the screw pocket 2104, (see FIG. 44) that can be straight when the pivot clamp 220 is placed in the channel 2102 but are that can be swaged or bent in area 2103 (see FIG. 41) to prevent the pivot clamp 210 from accidental displacement from the connector body 210 if the rod clamp 220 and clamp screw 240 are removed from the transverse connector sub-assembly 201. Prior to installing the pivot clamp 220 into the connector body 210 the spring shaft 250 can be inserted into the counter-bore 2205 and spring hole 2204 of the pivot clamp 220 (see FIG. 54). The spring shaft 250 is desirably sufficiently flexible to fit over the sides of the connector body 210 and drop into spring pocket 2105 (see FIG. 46) of the connector body (see FIG. 37). Those skilled in the art should understand that a hole (see spring hole 2115 in FIG. 135) or other feature can be used to retain the spring shaft 250 in position in lieu of the spring pocket 2105. With this arrangement, the pivot clamp 220 will now desirably rotate into the position shown in FIGS. 39 and 40 when the spring shaft 250 is in its normal, relaxed, position alongside wall 2106 (see FIG. 46).

In another embodiment of the transverse connector 22 (see FIGS. 134-137) the channel 2101 can be replaced with a through diameter 2111 in the connector body 211 and the pivot clamp can be a multiple piece assembly consisting of a pivot shaft 221A and pivot clamps 211B and 221C where the diameter 2211 of the pivot shaft 221A rotates in the through diameter 2111. The pivot clamps can be welded onto the pivot shaft at mating surfaces 2212 and 2213 but those skilled in the art should understand that there other methods and means of attachment such as interference fits, screws and/or bonding that are also within the scope of this invention.

Figure 35:
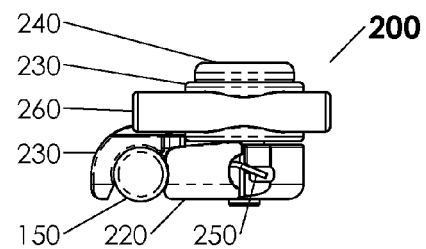
Figure 36:
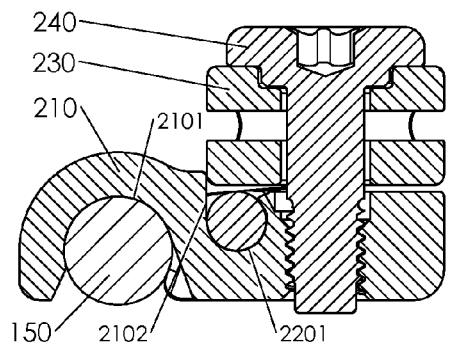
FIG. 36 depicts an enlarged section view of the transverse connector system of FIG. 34 taken along line P-P.
Figure 37:
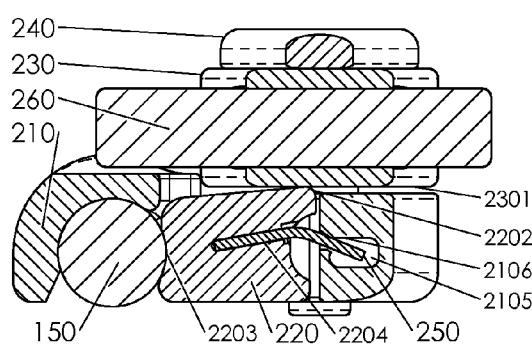
FIG. 37 depicts an enlarged section view of the transverse connector system of FIG. 34 taken along line I-I.
Figure 38:
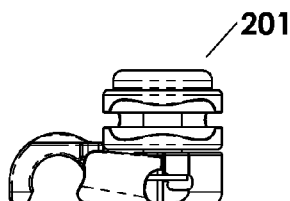
FIGS. 38 and 39 depict various planar views of a transverse connector sub-assembly, without an associated support rod and connector rod.

The surgeon can now take the complete transverse connector assembly 200 and snap the assembly onto the previously implanted support rods 150. This is accomplished by the presence of the support rod 150, which applies pressure to the flanges 2206 of the pivot clamp 220 and upon pressure from the surgeon's advancement of the assembly causes the pivot clamp 220 to rotate, thus flexing the spring shaft 250 as shown in FIGS. 35 and 37. In this orientation, the spring shaft 250 should now apply spring pressure to the pivot clamp 220, thereby allowing the rod to slide into and along the channel 2108 of the connector body 210 (see FIG. 46), which also desirably "pinches" and/or frictionally captures the support rod's diameter 1501 between radial surfaces 2203 and 2101 of the pivot clamp 220 and connector body 210 (at least partially due to the spring pressure from the spring rod 250—see FIG. 37), thus keeping the transverse connector sub-assemblies 201 in a desired position. Alignment of the transverse connector assembly 200 can be easily accomplished, as each transverse connector sub-assembly 201 can assume a variety of individual rotational axes X, Y and Z (see FIG. 74), thereby allowing an essentially infinite number of positions. FIGS. 71 through 74 demonstrate various exemplary contortion capabilities of the connection systems described herein.

Figure 63:
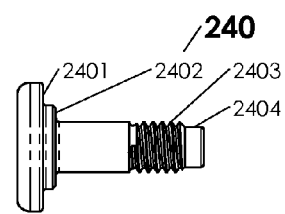
Figure 64:
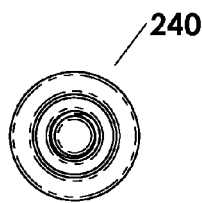
Figure 65:
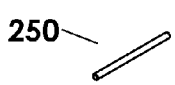
FIG. 65 depicts a perspective view of one embodiment of a spring shaft.
Figure 66:
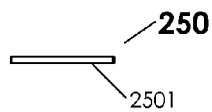
FIG. 66 depicts a side view of the spring shaft of FIG. 65.

Once various components of a transverse connector sub-assembly have been preassembled (but not tightened, if desired), the surgeon can easily slide various components of the transverse connector sub-assemblies 201 into a final desired position and/or orientation. Once the transverse connector assembly 200 is in place, the surgeon can tighten the clamp screw 240 on each subassembly, and the surface 2401 (see FIG. 63) will apply pressure to the rod clamp 230, thereby locking the connecting rod 260 in place while simultaneously applying further downward pressure onto the pivot clamp contact face 2301 (see FIG. 60) and pivot clamp lever arm radius 2202 (see FIG. 52), which locks the transverse connector sub-assemblies 201 onto the support rods 150. One exemplary final locked position is shown in FIG. 37.

Figure 43:
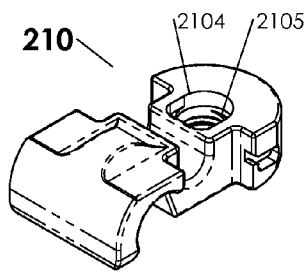
FIG. 43 depicts a perspective view of another embodiment of a connector body.
Figure 62:
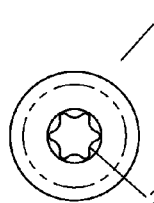
FIGS. 62-64 depict various planar views of the clamp screw of FIG. 61.
Figure 135:
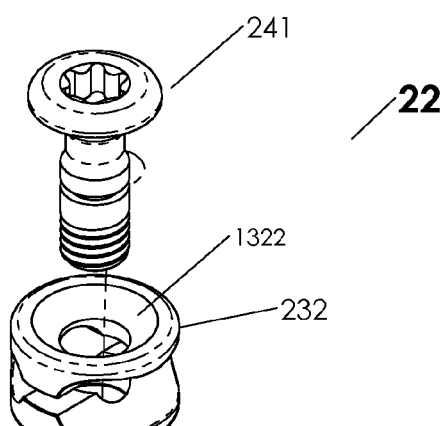
FIG. 135 is an exploded perspective view of the transverse connector of FIG. 134.
Figure 136:
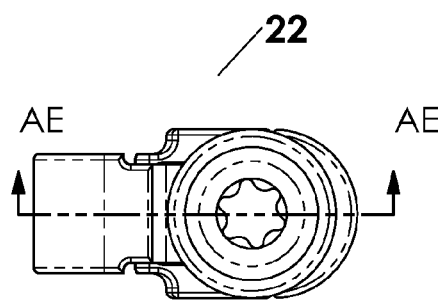
FIG. 136 is a top view of the transverse connector of FIG. 134.
Figure 137:
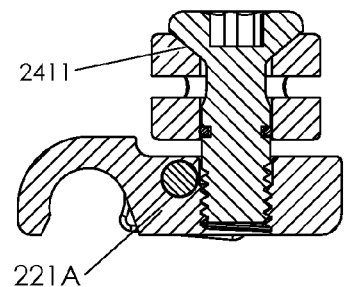
FIG. 137 is a cross-sectional view of the transverse connector of FIG. 136, taken along line AE-AE of FIG. 136.

If desired, a shoulder 2402 of the clamp screw 240 (see FIG. 63) can be provided that gives additional strength to the female hexalobe 2405 (should it be desired), which can fit into a counter-bore 2303 (see FIG. 60) of the rod clamp 230 when assembled. If desired, as shown in FIGS. 135 and 137, mating countersinks 1322 and 2411 can be used to reduce the height of the construct. If desired, there can also be pilot diameter 2404 on the clamp screw, if desired, to help align the male thread 2403 (see FIG. 63) and female thread 2105 (see FIG. 43) of the connector body 210. To those of ordinary skill in the art it should be understood that the various features 2402, 2404 and 2303 (see FIGS. 63 and 60) could be provided in various combinations (or need not be present, if desired) for the invention to perform as intended. It should also be understood that hexalobe 2405 (FIG. 62) or other features or shapes, like a hexalobe (Torx), square, slotted, cross or other shapes, could be utilized. It should be apparent to those skilled in the art that the spring ring 270 which is used to retain the rod clamp 232 on the screw 241 can be any number of various features such as bendable tabs or a pin in groove feature in order to retain the spring clamp 232 on the screw 241 while simultaneously allowing free rotation of the screw 241 in the rod clamp 232.

Figure 2:
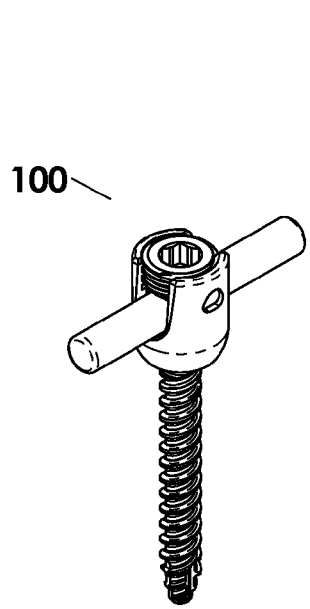
FIG. 2 depicts a perspective view of a subassembly of the pedicle screw system of FIG. 1.
Figure 3:
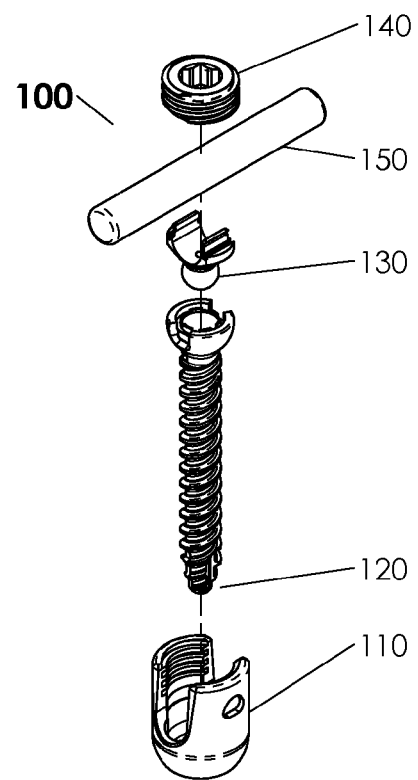
FIG. 3 depicts an exploded perspective view of the pedicle screw system subassembly of FIG. 2.
Figure 9:
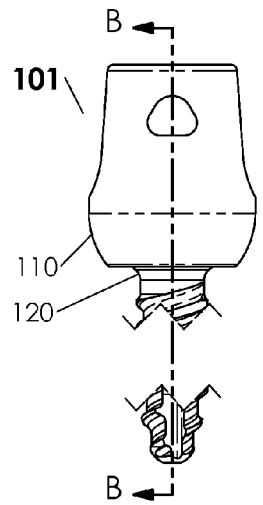
FIG. 9 depicts a broken front plan view of the pedicle-screw sub-assembly of FIGS. 4 and 5 with the set screw and support rod removed.

FIG. 2 depicts a side view of another additional embodiment of a single transverse connector assembly 300, where no spring shaft is provided, but the clamping and contortion features of the system are substantially similar to those previously described.

Figure 129:
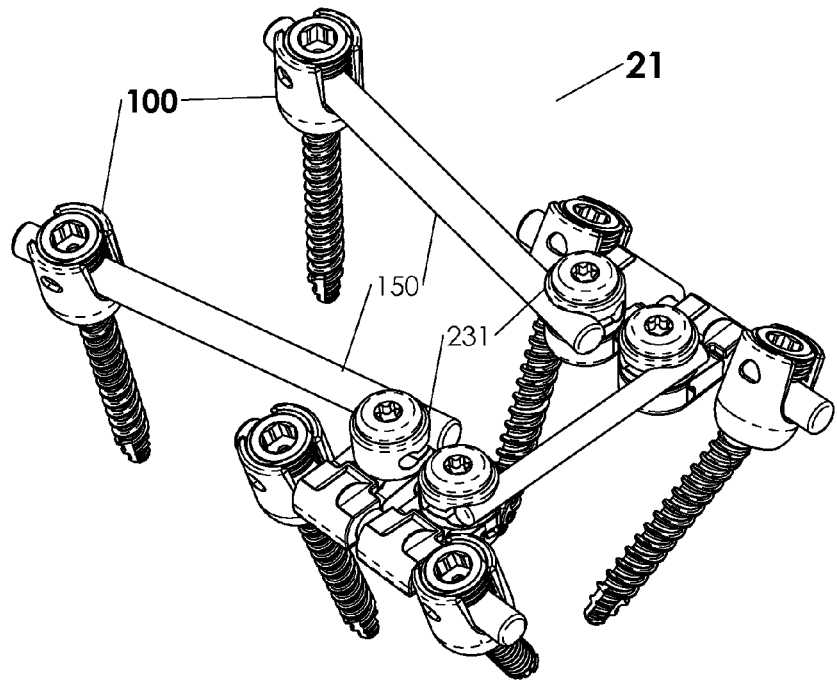
FIG. 129 depicts a perspective view of an implant system using an alternative extension embodiment of a transverse connector rod clamp.

FIG. 129 depicts another additional embodiment of a single transverse connector assembly 21, where a rod clamp 231 accepts a support rod and is used to extend a construct to additional levels without requiring disassembly of an existing construct and/or using a longer support rod. This embodiment would potentially be very useful in a revision surgery where the physician desires to attach additional pedicle screw assemblies 100 to a prior construct from an earlier surgery while leaving the implants from the original surgery in place.

FIGS. 84-91 depict another embodiment of a hook assembly 400 constructed in accordance with various teachings of the present invention, which includes hooks or other connection features to attach various components to bony members of the spine or other anatomical locations. Various disclosed components that could be utilized with this embodiment include a hook body 410 having a single hook 4102; a hook body 420 having a bifurcated hook 4203; an offset hook body 450 which could include various offsets 4501 and various hook forms (i.e., including bifurcated and/or single 4402 and/or other arrangements). In addition, the various embodiments can include a lower saddle 430 and a set screw 440, which facilitate attachment to a support rod 150.

Spinal surgeons have used various hook-based systems to attach to bony elements of the spine for many years, but positioning the hooks in place and them maintaining the positioning and/or alignment of the hooks in a specific location has often been difficult, if not impossible, using prior art systems. Various features of the disclosed hook assembly system 400 can employ similar friction retention and "snap fit" techniques onto a support rod 150 as the various pedicle screw embodiments described previously. For example, the lower saddle 430 of the hook assembly 400 can include similar flexible fingers 4304 formed as part of the lower saddle or insert 130 (see 1304 on FIG. 24), which can be designed and sized to squeeze a support rod 150 and hold the hook assembly 400 securely in place when it is placed onto the support rod. The flexible fingers 4304 can provide an audible and tactile feedback to the surgeon, if such as desired, when the support rod 150 "snaps" into the lower saddle 430 from spring pressure of the flexible fingers 4304. Those of ordinary skill in the art should understand that various features of the lower saddle 430 and/or the flexible 4304 fingers could be formed integrally into the hook body, without necessarily requiring an additional component such as the lower saddle 430. In the disclosed embodiments, once a hook assembly 400 is placed onto a rod, the friction and other resistance forces induced by the pressure of the flexible fingers 4304 will desirably retain and keep the rod from slipping in the lower saddle 430. Desirably, however, the resistance forces and/or pressure does allow the surgeon to easily move the lower saddle 430 to an optimal position relative to the rod, either using his fingers or with instruments attached to the sides of the hook body via a similar pocket design (or other connection feature) as described in connection with the attachment pockets 1105 on the tulip body 110. Once placed in a desired position and/or orientation, the surgeon can then place a set screw 440 to lock the hook in place.

Though not shown it is understood that the connecting rod 260 can be the same diameter as the support rod 150 to extend the system and attach additional pedicle screws.

ADDITIONAL ALTERNATIVE CONFIGURATIONS

Figure 103:
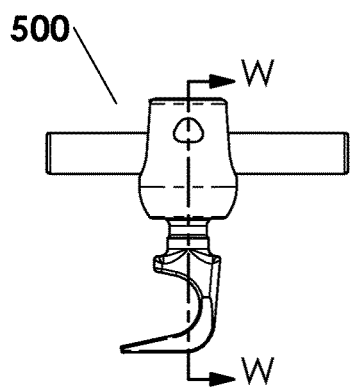
FIGS. 103 and 105 depict various views of an alternate embodiment of a poly-axial swiveling hook system.
Figure 104:
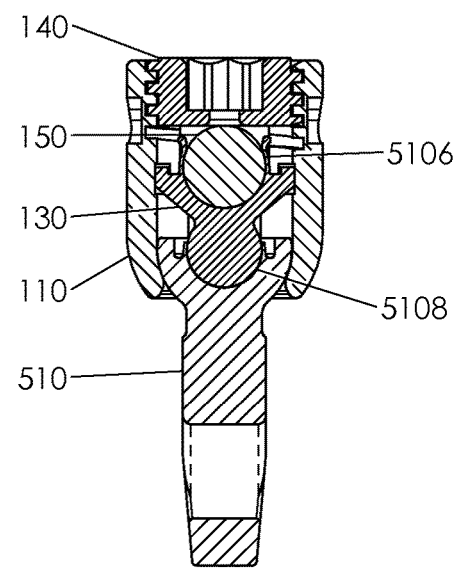
FIG. 104 depicts a cross-sectional view of the poly-axial swiveling hook system of FIG. 103, taken along line W-W.
Figure 105:
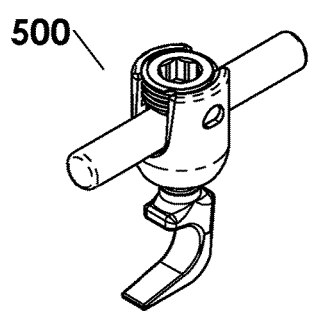

FIGS. 103-105 depict various views of one embodiment of a pivoting or swiveling hook pedicle screw hook system, which may comprise a tulip body 110, a lower saddle 130, a set screw 140 a support rod 150 and a swiveling hook 510. The swiveling hook 510 may include an inner surface receiver base 5108 that can receive the lower saddle insert 130, and/or at least one or more frictional elements or "fingers" 5106 which can desirably engage and/or inhibit relative motion between the lower saddle insert 130 and the receiver base 5108. Also, the swiveling hook may be adapted with a hook 5104, where the inner hook surface 5102 may be radiused to allow for anchoring to the targeted anatomy.

FIGS. 119-128 depict additional alternative embodiments of a polyaxial hook pedicle screw system constructed in accordance with various teachings of the present invention. FIGS. 119-121 depict another embodiment of a swiveling hook pedicle screw system 505, which may optionally include a swivel or pivot feature having a clevised or bifurcated tulip body 112 with an upper portion base 1122 and a lower portion base 1123. The lower portion base 1123 may include bifurcated arms 1121 that are distanced apart to form a channel or opening to receive the pivot head 5111 of the hook 511. The pivot head 5111 may be secured by means of a pivot pin 251. The hook assembly 505 can be retained on the support rod 150 by the flexible fingers of lower saddle 135.

In this embodiment, the pivot head 5113 and 5123 may be designed with smooth surfaces 5111 and 5112 (as shown in FIGS. 121 and 124 respectively) to allow for continuous and uninterrupted orientation and/or movement, or such surfaces may be textured to increase resistance to movement and/or securement on locked into position. In various alternative embodiments, the pivot head may include a variety of radiuses and/or configurations, such as a circular radius pivot head 5112 (as shown in FIG. 120) and/or an arched radius pivot 5121 (as shown in FIG. 123), where the arched radius 5121 may have a transition region or necked region 5124. When the set screw 140 is tightened in its final assembly, a downward force is desirably translated through the support rod 150, the lower saddle 136 and the arched pivoting hook 512.

In various alternative embodiments, the pivot head 5132 may include mechanized locking and/or "ratcheting" features to desirably control and/or limit the orientation and/or movement of the various components, such as shown in FIG. 128. FIGS. 125-128 depict one alternative embodiment of a polyaxial hook pedicle screw system 507 with a ratcheted pivot head 5132. The ratcheted polyaxial pedicle screw system 507 may also include a clevised and/or bifurcated tulip body 114, which desirably retains a pivotal hook 513 by means of a pivot pin 251. The ratcheted polyaxial hook pedicle screw system 507 can be retained on the support rod 150 by the flexible fingers of lower saddle 137. When the set screw 140 is tightened in its final assembly, a downward force is translated through the support rod 150, the lower saddle 137 and the ratcheted pivoting hook 513. The ratcheted pivoting hook 513 may be locked into various positions by female radial teeth 1371 of the lower saddle 136 and the mating male radial teeth 5131 of the pivot head 5132. The male radial teeth 5131 and the female radial teeth 1371 of the lower saddle 136 may be distanced apart to achieve a desired control of angle, orientation and/or movement. For example, the male radial teeth 5131 and the female radial teeth 1371 may have 1 mm, 2 mm, or 3 mm distance and/or angular measurements may be used (i.e., 5, 10, 15 or 20 degrees), which may be notched or printed on the pivot head 5132.

If desired, various features of the alternative embodiments of a polyaxial hook pedicle screw system, including those shown in FIGS. 119-128, may be designed by combining some or all the shapes, configurations and surfaces discussed above. For example, the ratcheted pivot head 5132 may be designed with a circular radius pivot head 5112 (as shown in FIG. 120) instead of an arched radius pivot head. The hook pedicle screw system may also include a uniaxial design as well.

All references, including publications, patent applications, and patents, cited herein are hereby incorporated by reference to the same extent as if each reference were individually and specifically indicated to be incorporated by reference and were set forth in its entirety herein.

The various headings and titles used herein are for the convenience of the reader, and should not be construed to limit or constrain any of the features or disclosures thereunder to a specific embodiment or embodiments. It should be understood that various exemplary embodiments could incorporate numerous combinations of the various advantages and/or features described, all manner of combinations of which are contemplated and expressly incorporated hereunder.

The use of the terms "a" and "an" and "the" and similar referents in the context of describing the invention are to be construed to cover both the singular and the plural, unless otherwise indicated herein or clearly contradicted by context. The terms "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., i.e., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventor for carrying out the invention. Variations of those preferred embodiments may become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context

The invention claimed is:

1. A bone anchor assembly, comprising:
 a fixation element configured to couple to a bone, the fixation element having a lower bone-engaging portion for engaging an outer surface of the bone and an upper head portion, the upper head portion including an inwardly curved recessed portion and a generally hemispherical outer portion, the fixation element further connected to an upper housing portion having an internal bore extending there through, the housing portion having at least two sidewalls forming a first channel adapted to receive a connecting rod; and an insert sized and configured for insertion into the internal bore of the housing portion, the insert having an upper receiver portion for making an upper provisional connection to the connecting rod and a lower generally hemispherical portion for engaging with the inwardly curved recessed portion of the upper head portion, wherein the upper receiver portion includes a plurality of flexible fingers extending upwardly from the insert, at least two of the flexible fingers being spaced apart a first distance at a location distal from the insert, the first distance being less than a diameter of the connecting rod.

2. The bone anchor assembly of claim 1, wherein the upper receiving portion making the upper provisional connection selectively retains the connecting rod within the first channel but allows the connecting rod to slide along a longitudinal axis of the connecting rod within the first channel of the housing portion.

3. The bone anchor assembly of claim 1, wherein advancement of a set screw into the housing converts the upper provisional connection into an upper permanent connection, whereby the upper permanent connection inhibits relative movement between the insert and the connecting rod.

4. The bone anchor assembly of claim 1, wherein the insert includes a plurality of anchoring tabs projecting outward from a generally cylindrical periphery of the insert, the anchoring tabs sized and configured to engage with a plurality of pockets formed into an inner surface of the housing portion when the insert is assembled to a desired position within the housing portion.

5. The bone anchor assembly of claim 1, wherein the lower bone-engaging portion comprises a hook element adapted to hook onto the bone.

6. The bone anchor assembly of claim 1, wherein the lower bone-engaging portion is integrally formed with the upper housing portion.

7. The bone anchor assembly of claim 1, wherein a monoaxially-adjustable connection is positioned between the lower bone-engaging portion and the upper housing portion.

8. The bone anchor assembly of claim 1, wherein a polyaxially-adjustable connection is positioned between the lower bone-engaging portion and the upper housing portion.

9. A surgical construct comprising:
a fixation element configured to couple to a bone, the fixation element having a head portion and a hook-shaped element for engaging an outer surface of the bone, the head portion including a curved outer surface with a generally flat upper portion, the generally flat upper portion including a recess formed therein;
a rod holding body for accommodating at least a portion of a connecting rod, the rod holding body including a lower opening, a chamber and a threading area, the lower opening sized and configured to accommodate at least a portion of the head portion;
an insert sized and configured to fit within the chamber, the insert including a central body, an upper rod receiving portion and a lower head engaging portion;
the upper rod receiving portion including at least two rod fingers extending distally upward from the central body, a spacing between the at least two rod fingers at a location distal from the central body being less than an outer diameter of the connecting rod such that, when the connecting rod is positioned within the rod receiving portion, the rod fingers contact the connecting rod with sufficient frictional force to inhibit but not preclude movement of the rod relative to the upper rod receiving portion; and
the lower head engaging portion including a lower curved surface for engaging an upwardly curved surface within the recess of the head portion of the fixation element with sufficient frictional force to inhibit but not preclude movement of the fixation element relative to the lower head engaging portion.

10. The surgical construct of claim 9, wherein the central body of the insert is formed in a generally concentric cylindrical shape, and the chamber of the rod holding body is formed in a generally non-concentric cylindrical shape.

11. The surgical construct of claim 9, wherein the insert further comprises at least one securement tab extending outward from the central body, the securement tab sized and configured to engage with at least one pocket formed in an inner surface of the chamber.

12. The surgical construct of claim 9, wherein the lower curved surface comprises a first textured portion configured for engagement with a corresponding second textured portion of the upwardly curved surface of the recess.

13. The surgical construct of claim 9, wherein the fixation element is monoaxially-adjustable relative to the rod holding body.

14. The surgical construct of claim 9, wherein the fixation element is polyaxially-adjustable relative to the rod holding body.

15. The surgical construct of claim 9, wherein advancement of a set screw into the threading area rigidly connects the connecting rod to the rod holding body and rigidly connects the rod holding body to the fixation element.

16. The surgical construct of claim 9, wherein at least one of the at least two rod fingers is flexible.

17. A surgical construct comprising:
a fixation element configured to couple to a bone, the fixation element having a head portion and a hook-shaped element for engaging an outer surface of the bone, the head portion including a recess formed therein, the recess including a hemispherical inner wall;
a rod holding body for accommodating at least a portion of a connecting rod, the rod holding body including a lower opening, a chamber and a threading area, the lower opening sized and configured to accommodate at least a portion of the head portion;
an insert sized and configured to fit within the chamber, the insert including a central body, an upper rod receiving portion and a lower head engaging portion;
the upper rod receiving portion including a plurality of rod fingers extending distally upward from the central body, a spacing between at least two of the plurality of rod fingers at a location distal from the central body being less than an outer diameter of the connecting rod such that, when the connecting rod is positioned within the rod receiving portion, the plurality of rod fingers contact the connecting rod with sufficient frictional force to inhibit but not preclude movement of the rod relative to the upper rod receiving portion;

the lower head engaging portion including a lower surface sized to extend at least partially within the recess for engaging the hemispherical inner wall of the recess.

18. The surgical construct of claim 17, wherein the fixation element is configured for monoaxial movement relative to the rod holding body.

19. The surgical construct of claim 17, wherein the fixation element is configured for polyaxial movement relative to the rod holding body.

* * * * *